(12) United States Patent
Shimamura et al.

(10) Patent No.: US 10,977,793 B2
(45) Date of Patent: Apr. 13, 2021

(54) DYNAMIC ANALYSIS APPARATUS, DYNAMIC ANALYSIS SYSTEM, AND STORAGE MEDIUM

(71) Applicant: Konica Minolta, Inc., Tokyo (JP)

(72) Inventors: Kenta Shimamura, Hino (JP); Noritsugu Matsutani, Musashino (JP)

(73) Assignee: KONICA MINOLTA, INC., Tokyo (JP)

( * ) Notice: Subject to any disclaimer, the term of this patent is extended or adjusted under 35 U.S.C. 154(b) by 0 days.

(21) Appl. No.: 16/833,808

(22) Filed: Mar. 30, 2020

(65) Prior Publication Data

US 2020/0327665 A1   Oct. 15, 2020

(30) Foreign Application Priority Data

Apr. 10, 2019   (JP) .............................. JP2019-074999

(51) Int. Cl.
| | | |
|---|---|---|
| *G08B 23/00* | (2006.01) | |
| *G06T 7/00* | (2017.01) | |
| *A61B 5/113* | (2006.01) | |
| *A61B 5/11* | (2006.01) | |
| *G06T 7/13* | (2017.01) | |
| *G06T 11/60* | (2006.01) | |
| *G06T 7/215* | (2017.01) | |
| *A61B 6/00* | (2006.01) | |

(52) U.S. Cl.
CPC ............ *G06T 7/0012* (2013.01); *A61B 5/113* (2013.01); *A61B 5/1128* (2013.01); *G06T 7/13* (2017.01); *G06T 7/215* (2017.01); *G06T 11/60* (2013.01); *A61B 6/50* (2013.01); *G06T 2207/30061* (2013.01); *G06T 2207/30096* (2013.01)

(58) Field of Classification Search
CPC ......... G06T 7/0012; G06T 2207/80061; G06T 7/174; G06T 11/60; G06T 7/13; G06T 2207/20208; A61B 5/08; A61B 5/082; A61B 6/463; A61B 5/1128; A61B 5/113
See application file for complete search history.

(56) References Cited

U.S. PATENT DOCUMENTS

| 8,403,861 B2 * | 3/2013 | Williams | ............... A61B 5/082 600/532 |
| 2015/0073257 A1 * | 3/2015 | Muraoka | ............. A61B 6/4266 600/407 |

FOREIGN PATENT DOCUMENTS

JP   2016-214725 A   12/2016

* cited by examiner

*Primary Examiner* — Toan N Pham
(74) *Attorney, Agent, or Firm* — Lucas & Mercanti, LLP

(57) ABSTRACT

A dynamic analysis apparatus includes a hardware processor. The hardware processor is configured to perform the following, calculate a prediction rate multiplied by a respiratory function value of the subject in predicting the respiratory function value when an exclusion target portion is excluded; obtain input of the exclusion target portion in an anatomical unit from the input unit, based on the anatomical unit, specify a partial region of the lung field in which a characteristic amount relating to a respiratory function in the plurality of frame images is calculated, calculate the characteristic amount related to the respiratory function in the partial region of the lung field specified from the plurality of frame images and the characteristic amount related to the respiratory function of an entire lung field, and calculate the prediction rate based on a characteristic amount ratio which is a ratio of the two calculated characteristic amounts.

15 Claims, 11 Drawing Sheets

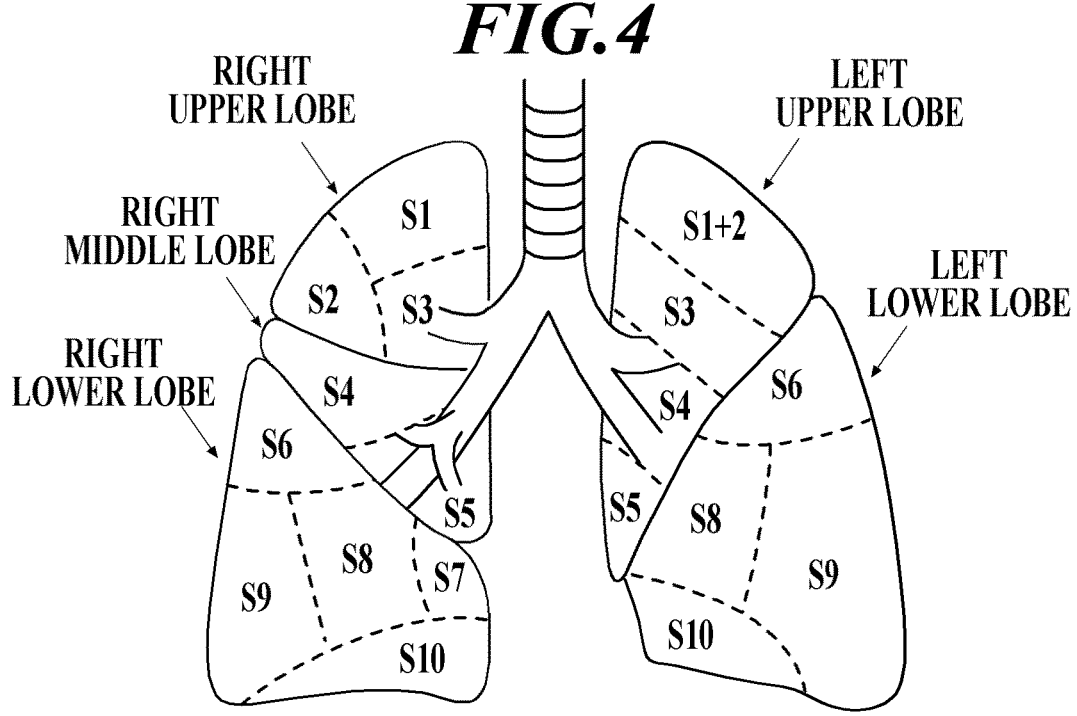

| ANATOMICAL UNIT | LUNG SIZE VALUE |
|---|---|
| RIGHT LUNG | 10 |
| LEFT LUNG | 9 |
| RIGHT UPPER LOBE | 3 |
| RIGHT MIDDLE LOBE | 2 |
| RIGHT LOWER LOBE | 5 |
| ⋮ | ⋮ |

321

DYNAMIC ANALYSIS APPARATUS, DYNAMIC ANALYSIS SYSTEM, AND STORAGE MEDIUM

CROSS-REFERENCE TO RELATED APPLICATIONS

The entire disclosure of Japanese Patent Application No. 2019-074999 filed on Apr. 10, 2019 is incorporated herein by reference in its entirety.

BACKGROUND

Technological Field

The present invention relates to a dynamic analysis apparatus, a dynamic analysis system, and a storage medium.

Description of the Related Art

Lung cancer operation has been performed more than 30,000 times a year in Japan, and although the mortality rate has decreased in recent years, it is an operation with a high risk of complications. When the operation of lung cancer is applied, the physician decides the operation plan such as whether or not to carry out the operation or to carry out the reduction operation by comprehensively carrying out the risk judgment in consideration of the risk judgment value in accordance with the guideline and various other factors before the operation. An important component of this risk judgment value is the prediction of postoperative respiratory function. Postoperative respiratory function not only affects the results of risk judgment according to the guideline, but is also strongly associated with the occurrence of complications, and it is important to grasp this accurately.

If lung cancer is present, there are options such as drug treatment, but resection is effective as a radical cure and surgical resection of lung cancer is recommended if possible. Lung cancer resection is often performed by resection in a unit of a lung lobe, although in some cases one of the right or left lungs lung is completely removed. If the resection is to leave as much of the lung as possible after the operation, it is also an option to perform the resection at a lung region level smaller than the lung lobes, referred to as a reduction operation. However, even if reduction operation is performed, there is a possibility that cancer already spread to nearby lung regions. Therefore, it is advisable to remove lung lobes from the view point of curing radically. One of the criteria for judging whether or not operation itself can be performed and whether or not reduction operation is performed is the prediction of the respiratory function after operation. If the predicted value of the respiratory function after operation is not more than a predetermined threshold, even if the person is aiming for a radical cure, the risk of complications, etc. is high. Therefore it may be judged that reduction operation is the only possible operation or that operation itself should not be performed. Improving the predictive accuracy of postoperative respiratory function increases the accuracy of postoperative risk judgment, and therefore, if the postoperative risk is determined to be low, lobectomy rather than regional resection can be selected to facilitate radical cure. In addition, when it is judged that the risk after the operation is high, it is possible to make an accurate judgment that the reduction operation should be performed or the operation should be stopped in order to reduce the risk.

As a method for predicting the respiratory function after the operation, there is a technique using pulmonary blood flow scintigraphy examination. However, pulmonary blood flow scintigraphy examination can only be held in a relatively large hospital and cannot be used in a small hospital because the examination apparatus is large and expensive. Also in facilities with scintigraphy examination equipment, the subject must usually wait about one week after ordering the scintigraphy examination in order to manage radioisotopes. Since the exposure amount is large, the examination is used for only high-risk patients. Therefore, the risk of complications could not be accurately grasped for many patients. In addition, in the pulmonary blood flow scintigraphy examination, since only the right and left blood flow images are obtained, the position of the lung cannot be accurately grasped, and it is difficult to accurately predict the respiratory function.

As a technique for solving these problems, for example, JP 2016-214725 proposes a technique for predicting the respiratory function after operation using an X-ray dynamic image. Specifically, it is described that, when a user selects a region corresponding to a pulmonary resection range from an image by an operation on an operation unit or the like, a characteristic amount in a region excluding a selected region from the entire lung field in a dynamic image of the chest, a characteristic amount in the entire lung field, and a ratio of the characteristic amount in a region excluding the selected region from the entire lung field and the characteristic amount in the entire lung field are calculated, and the result of the examination of the spirometry examination is multiplied to the above, thereby predicting the respiratory function value after the pulmonary resection.

However, in the technique described in JP 2016-214725, although it is necessary for the user to designate an exclusion target region to be excluded by resection from the lung on the dynamic image, the accuracy and reproducibility are poor, and there is a burden on the user.

SUMMARY

An object of the present invention is to easily and accurately designate a place to be excluded when a respiratory function value in a case where a part of a lung is excluded is predicted using a chest dynamic image.

To achieve at least one of the abovementioned objects, according to an aspect of the present invention, a dynamic analysis apparatus reflecting one aspect of the present invention comprises: a hardware processor configured to analyze a plurality of frame images showing a dynamic state of a chest portion of a subject and which calculates a prediction rate multiplied by a respiratory function value of the subject in predicting the respiratory function value when an exclusion target portion which is a portion of a lung field of the subject is excluded; and an input unit, wherein, the hardware processor obtains input of the exclusion target portion in an anatomical unit from the input unit, based on the anatomical unit obtained from the input unit, the hardware processor specifies a partial region of the lung field in which a characteristic amount relating to a respiratory function in the plurality of frame images is calculated, the hardware processor calculates the characteristic amount related to the respiratory function in the partial region of the lung field specified from the plurality of frame images and the characteristic amount related to the respiratory function of an entire lung field, and the hardware processor calculates the prediction rate based on a characteristic amount ratio which is a ratio of the two calculated characteristic amounts.

According to another aspect of the present invention, a dynamic analysis system comprises: an imaging apparatus which performs radiography on the subject to obtain a plurality of frame images showing a dynamic state of a chest portion of the subject; and a dynamic analysis apparatus according to claim 1.

According to another aspect of the present invention, a non-transitory computer-readable storage medium stores a program which controls a computer used in a dynamic analysis apparatus the program which controls the computer to perform: analyzing a plurality of frame images showing a dynamic state of a chest portion of a subject, calculating a prediction rate multiplied to a respiratory function value of the subject in predicting the respiratory function value when an exclusion target portion which is a portion of a lung field of the subject is excluded, obtaining input of the exclusion target portion in an anatomical unit, based on the obtained anatomical unit, specifying a partial region of the lung field in which a characteristic amount relating to a respiratory function in the plurality of frame images is calculated, calculating the characteristic amount related to the respiratory function in the partial region of the lung field specified from the plurality of frame images and the characteristic amount related to the respiratory function of an entire lung field, and calculating the prediction rate based on a characteristic amount ratio which is a ratio of the two calculated characteristic amounts.

BRIEF DESCRIPTION OF THE DRAWINGS

The advantages and features provided by one or more embodiments of the invention will become more fully understood from the detailed description given hereinbelow and the appended drawings which are given by way of illustration only, and thus are not intended as a definition of the limits of the present invention, wherein:

FIG. 4 is a diagram showing anatomical units constituting a lung;

FIGS. 5A, 5B, and 5C illustrate an example of a user interface to input an exclusion target portion from the lung field;

DETAILED DESCRIPTION OF THE EMBODIMENTS

Hereinafter, one or more embodiments of the present invention will be described with reference to the drawings. However, the scope of the invention is not limited to the disclosed embodiments.

[Configuration of the Dynamic Analysis System 100]

First, the configuration of the present embodiment will be described.

Figure 1:
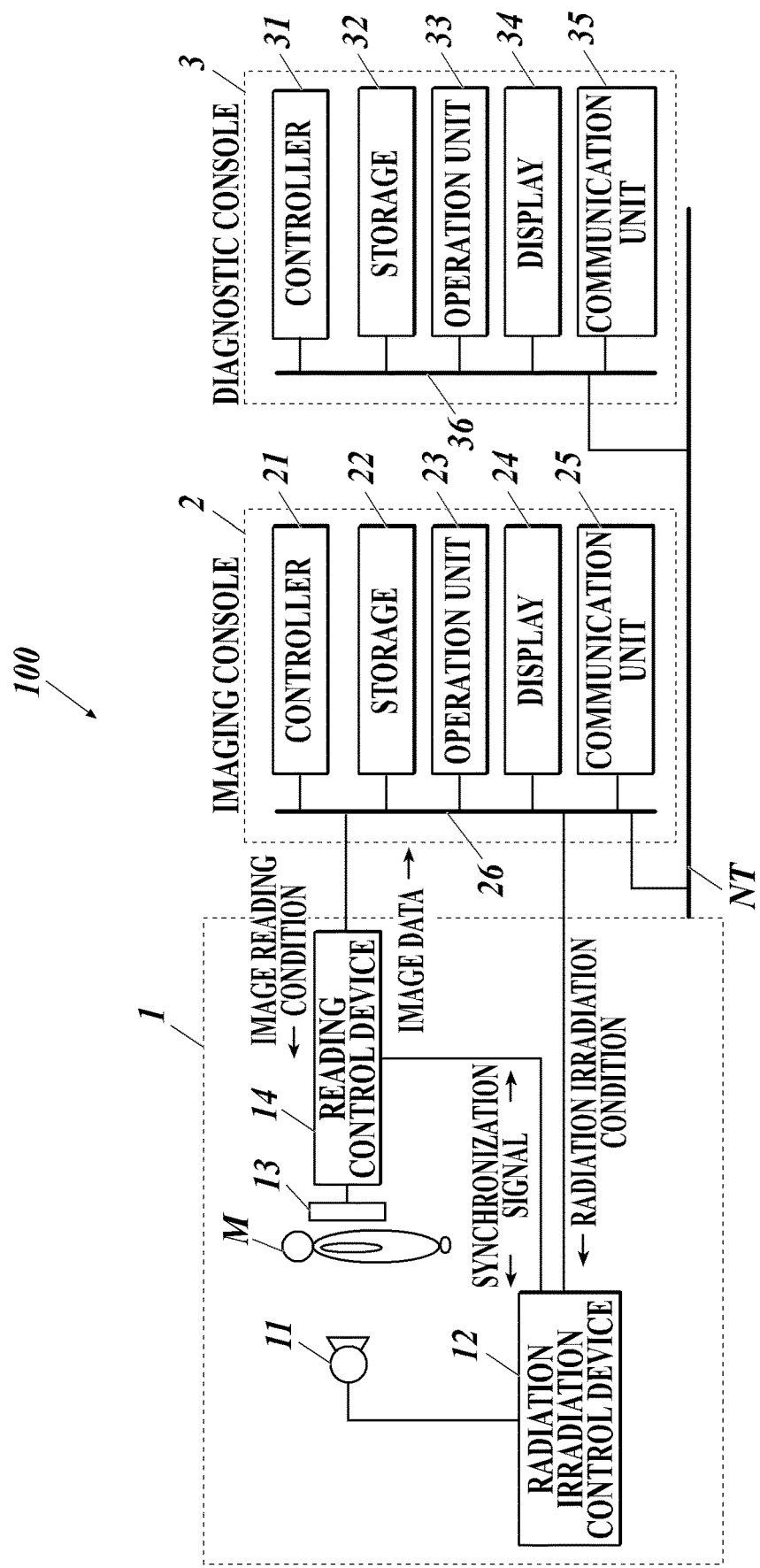
FIG. 1 is a diagram showing an overall configuration of a dynamic analysis system according to an embodiment of the present invention.

FIG. 1 shows an overall configuration of a dynamic analysis system 100 according to the present embodiment.

As shown in FIG. 1, in the dynamic analysis system 100, an imaging device 1 and an imaging console 2 are connected by communication cables or the like, and an imaging console 2 and a diagnostic console 3 are connected via a communication network NT such as a LAN (Local Area Network). The devices constituting the dynamic analysis system 100 conform to DICOM (Digital Image and Communications in Medicine) standard, and the communication between the devices is performed in accordance with DICOM.

[Configuration of the Imaging Device 1]

The imaging apparatus 1 is an imaging unit for imaging chest dynamics having periodicity (cycles), such as changes in the form of lung expansion and contraction due to respiratory movement, heart beats, and the like. Dynamic radiography refers to obtaining a plurality of images showing dynamics of a subject by repeatedly irradiating the subject with radiation such as X-rays in pulses at predetermined time intervals (pulsed irradiation) or by continuously irradiating a subject at a low dose rate (continuous irradiation). The series of images obtained by the dynamic imaging is called a dynamic image. Each of the plurality of images forming the dynamic image is referred to as a frame image. In the following embodiment, a case where dynamic imaging of the front of the chest is performed by pulsed irradiation will be described as an example.

The radiation source 11 is disposed at a position facing the radiation detector 13 with the subject M (subject) interposed therebetween, and irradiates the subject M with radiation (X-rays) under the control of the radiation irradiation control device 12.

The radiation irradiation control device 12 is connected to the imaging console 2, and performs radiography by controlling the radiation source 11 based on the radiation irradiation conditions input from the imaging console 2. Radiation irradiation conditions input from the imaging console 2, for example, the pulse rate, pulse width, pulse interval, the number of imaging frames per imaging, the value of the X-ray tube current, the value of the X-ray tube voltage, the additional filter type and the like. The pulse rate is the number of times of irradiation per second, and matches with a frame rate described later. The pulse width is the irradiation time per irradiation. The pulse interval is a time from the start of one irradiation to the start of the next irradiation, and matches with a frame interval to be described later.

The radiation-detecting unit 13 is a semiconductor image sensor such as a FPD (Flat Panel Detector). The FPD has, for example, a glass substrate or the like, and a plurality of detection elements (pixels) for detecting radiation irradiated from the radiation source 11 and transmitted through at least the subject M in accordance with the intensity of the radiation, converting the detected radiation into an electric signal, and accumulating the converted radiation are arranged in a matrix form at predetermined positions on the substrate. Each pixel includes a switching unit such as a TFT (Thin Film Transistor), for example. The FPD may be an indirect conversion type in which X-rays are converted into electric signals by a photoelectric conversion element via a scintillator, or a direct conversion type in which X-rays are directly converted into electric signals, and either type may be used.

The radiation detector 13 is provided so as to face the radiation source 11 with the subject M interposed therebetween.

The reading control device 14 is connected to the imaging console 2. The reading control device 14 controls the switching unit of each pixel of the radiation detector 13 based on the image reading condition input from the imaging console 2, switches reading of the electric signal accumulated in each pixel, and acquires image data by reading the electric signal accumulated in the radiation detector 13. This image data is a frame image. Then, the reading control device 14 outputs the acquired frame image to the imaging console 2. The image reading conditions include, for example, a frame rate, a frame interval, a pixel size, and an image size (matrix size). The frame rate is the number of frame images acquired per second and matches with the pulse rate. The frame interval is a time from the start of the acquisition operation of one frame image to the start of the acquisition operation of the next frame image, and matches with the pulse interval.

Here, the radiation irradiation control device 12 and the reading control device 14 are connected to each other, and synchronize the radiation irradiation operation and the image reading operation by exchanging a synchronization signal with each other.

[Configuration of Imaging Console 2]

The imaging console 2 outputs radiation irradiation conditions and image reading conditions to the imaging apparatus 1 to control radiography and radiographic image reading operations by the imaging apparatus 1, and displays dynamic images acquired by the imaging apparatus 1 for confirmation of positioning by an operator such as a radiography technician or for confirmation of whether or not the image is suitable for diagnosis.

As shown in FIG. 1, the imaging console 2 includes a controller 21, a storage 22, an operation unit 23, a display 24, and a communication unit 25, and the respective units are connected by a bus 26.

The controller 21 includes a central processing unit (CPU), a random access memory (RAM), and the like. The CPU of the controller 21 reads out a system program and various processing programs stored in the storage 22 in accordance with the operation of the operation unit 23, deploys them in the RAM, executes various processing including an imaging control process described later in accordance with the deployed program, and centrally controls the operation of each unit of the imaging console 2, and the radiation irradiation operation and the reading operation of the imaging apparatus 1.

The storage 22 is configured by including a nonvolatile semiconductor memory, a hard disk, and the like. The storage 22 stores various programs executed by the controller 21, parameters necessary for execution of processing by the programs, data such as processing results, and the like. For example, the storage 22 stores a program for executing the imaging control process shown in FIG. 2. The storage 22 stores radiation irradiation conditions and image reading conditions in association with the inspection target part and the imaging direction. The various types of programs are stored in a form of readable program code, and the controller 21 sequentially executes the operation according to the program code.

The operation unit 23 includes a keyboard including cursor keys, numeric input keys, various function keys, and the like, and a pointing device such as a mouse, and outputs instruction signals input by key operations on the keyboard or mouse operations to the controller 21. The operation unit 23 may include a touch panel on the display screen of the display 24. In this case, an instruction signal input via the touch panel is output to the controller 21.

The display 24 includes a monitor such as LCD (Liquid Crystal Display) and CRT (Cathode Ray Tube), and displays input instructions, data, and the like from the operation unit 23 in accordance with instructions of display signals input from the controller 21.

The communication unit 25 includes a LAN adapter, modem, TA (Terminal Adapter), and the like, and controls data transmission and data reception with devices connected to the communication network NT.

[Configuration of Diagnostic Console 3]

The diagnostic console 3 is a device which acquires a dynamic image from the imaging console 2, and predicts a respiratory function value after a lung resection operation in which a part of the lung is excluded by resection based on the acquired dynamic image.

As shown in FIG. 1, the diagnostic console 3 includes a controller 31, a storage 32, an operation unit 33, a display 34, and a communication unit 35, and the respective units are connected by a bus 36.

The controller 31 includes a CPU, a RAM, and the like. The CPU of the controller 31 reads out a system program and various processing programs stored in the storage 32 in accordance with the operation of the operation unit 33, deploys them in the RAM, executes various processing such as respiratory function prediction processing, which will be described later, in accordance with the deployed program, and centrally controls the operation of each unit of the diagnostic console 3. The controller 31 functions as a prediction rate calculating unit, respiration function value acquiring unit, prediction unit, correction unit, control unit, and acquiring unit.

The storage 32 is configured by including a nonvolatile semiconductor memory, a hard disk, and the like. The storage 32 stores various programs including a program for executing respiratory function prediction processing in the controller 31, and data such as parameters necessary for executing processing by the program, processing results, and the like. The various types of programs are stored in a form of a readable program code, and the controller 31 sequentially executes the operation according to the program code.

The storage 32 stores dynamic images imaged in the past and predicted results of respiratory function values after the operation in association with patient information (e.g., patient ID, patient name, height, weight, age, sex, etc.), and examination information (e.g., examination ID, examination date, examination target part (here, chest), and imaging direction (front, side surface)).

Figures 6, 7:
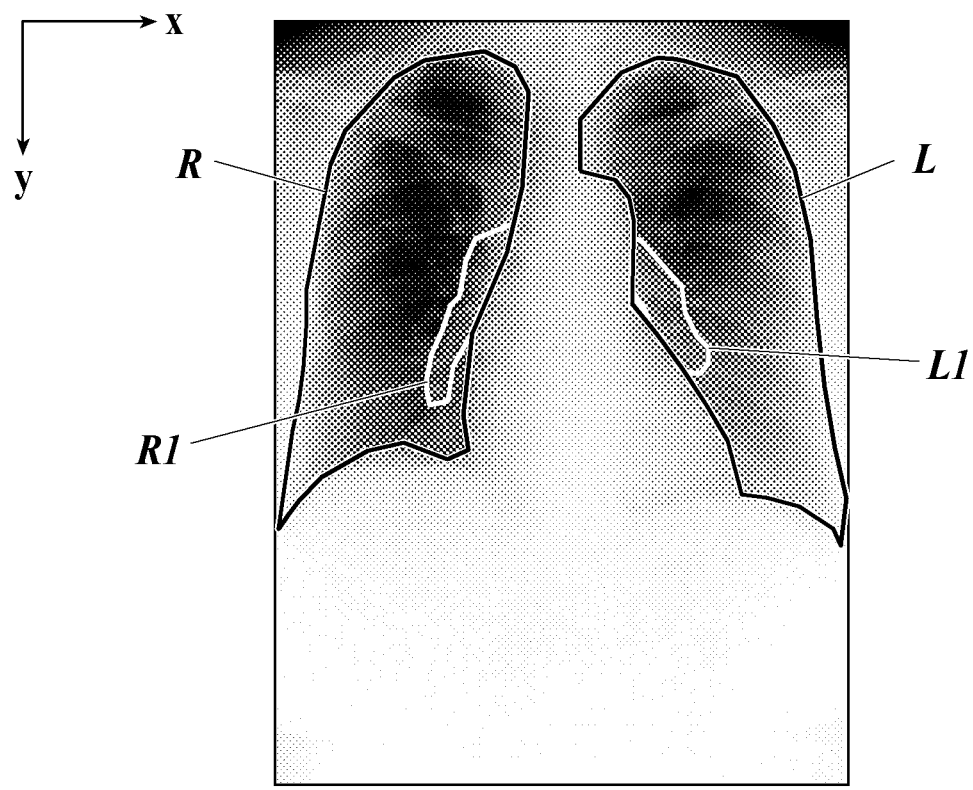
FIG. 6 is a diagram showing an example of a lung size value table.
FIG. 7 is a diagram showing a lung field region and hilar region.

The storage 32 stores a lung size value table 321 shown in FIG. 6. The lung size value table 321 is a table storing lung size values for each anatomical unit constituting the lung. Details will be described later.

The operation unit 33 is configured by including a keyboard including a cursor key, numeral input keys, various function keys and the like, and a pointing device such as a mouse. An instruction signal input by a key operation on the keyboard and a mouse operation performed by the user is output to the controller 31. The operation unit 33 may include a touch panel on the display screen of the display 34. In this case, an instruction signal input via the touch panel is output to the controller 31.

The operation unit 33 functions as an input unit in cooperation with the controller 31. It also functions as an operation unit.

The display 34 is configured by a monitor such as an LCD or a CRT, and performs various displays in accordance with an instruction of a display signal input from the controller 31.

The communication unit 35 includes a LAN adapter, a modem, a TA, and the like, and controls data transmission and reception with each device connected to the communication network NT.

[Operation of the Dynamic Analysis System 100]

Next, the operation of the dynamic analysis system 100 according to the present embodiment will be described.

(Operation of the Imaging Device 1 and the Imaging Console 2)

First, the imaging operation by the imaging apparatus 1 and the imaging console 2 will be described.

Figure 2:
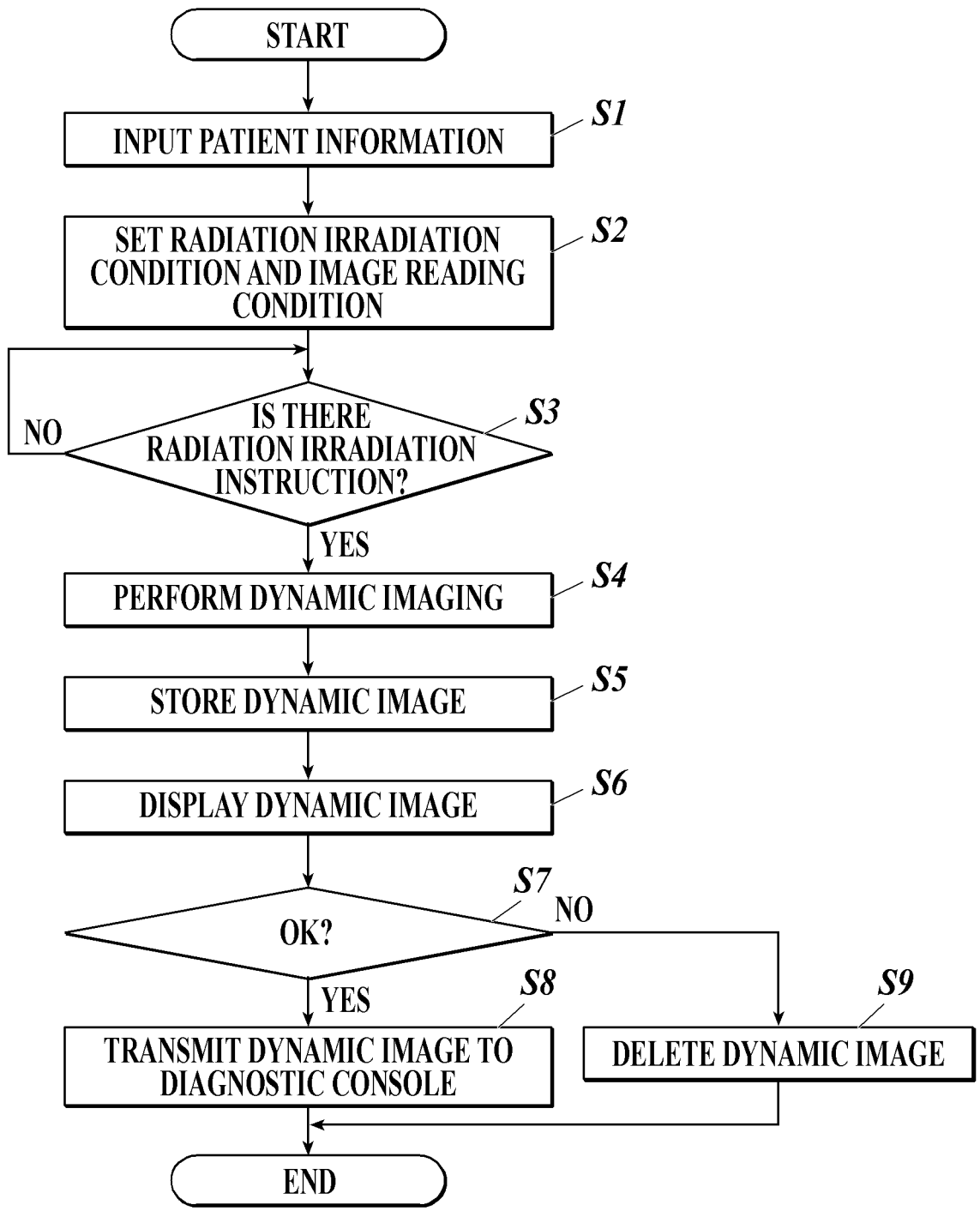
FIG. 2 is a flowchart showing an imaging control process executed by a controller of the imaging console shown in FIG. 1.

FIG. 2 shows an imaging control process executed by the controller 21 of the imaging console 2. The imaging control process is executed in coordination with the controller 21 and the program stored in the storage 22.

First, the operator operates the operation unit 23 of the imaging console 2 to input patient information and examination information of the subject (subject M) (step S1).

Next, the radiation irradiation conditions are read out from the storage 22 and set in the radiation irradiation control device 12, and the image reading conditions are read out from the storage 22 and set in the reading control device 14 (step S2).

Next, the device stands by for an instruction to irradiate radiation by the operation of the operation unit 23 (step S3). Here, the person who performs imaging positions the subject M by arranging the subject M between the radiation source 11 and the radiation detector 13. When the preparation for imaging is completed, the operation unit 23 is operated to input a radiation irradiation instruction.

When a radiation irradiation instruction is input by the operation unit 23 (step S3; YES), an imaging start instruction is output to the radiation irradiation control device 12 and the reading control device 14, and dynamic imaging is started (step S4). That is, radiation is irradiated by the radiation source 11 at pulse intervals set in the radiation irradiation control device 12, and a frame image is acquired by the radiation detector 13. During the dynamic imaging, the operator performs respiration guidance or breath hold instructions such as "breathe in," "breathe out," "hold breath," or the like, for example. Note that the imaging apparatus 1 may include an audio output unit or a display, and when an imaging start instruction is output, voice or display of respiration guidance or breath hold instruction such as "breathe in", "breathe out" or "hold breath" may be performed.

When a radiation irradiation end instruction is input by the operation unit 23, the controller 21 outputs an instruction to end imaging to the radiation irradiation control device 12 and the reading control device 14, and the imaging operation is stopped.

The frame images acquired by imaging are sequentially input to the imaging console 2, stored in the storage 22 in association with a number (frame number) indicating the imaging order (step S5), and displayed on the display 24 (step S6). The operator confirms the positioning or the like based on the displayed dynamic image, and determines whether an image suitable for diagnosis has been acquired by imaging (imaging OK) or re-imaging is necessary (imaging NG). Then, the operation unit 23 is operated to input the determination result.

Here, since the accuracy of the blood flow characteristic amount in the respiratory function prediction process in the subsequent stage is deteriorated when the motion of the subject M during imaging or the movement of the subject M due to respiration is large, it is desirable to measure the magnitude of the subject movement noise in step S6, and to display a warning urging the imaging technician to re-image on the display 24 when it is equal to or larger than a predetermined threshold value. The magnitude of the subject motion noise may be measured by calculating the number of pixels (areas) in which the pixel value change in the temporal direction is equal to or larger than a predetermined threshold value with respect to the entire image or the ROI set on the subject, or by numerically measuring the frequency component value (power spectrum or the like) in the vicinity of the heartbeat frequency and in the range of frequencies lower than the heartbeat frequency, or by other methods.

When the warning is displayed, in order to enable the operator to judge the necessity of re-imaging, it is desirable to display the numerical value itself showing the subject motion noise or the threshold value together with the temporal and spatial position where the subject motion noise was large. In the case of re-imaging, it is also necessary to grasp how to correct the breath holding method of the patient. For example, by indicating the temporal position where the subject motion noise was large, it is possible to judge whether the movement before and after breath holding was problematic or whether the body wobble during breath holding was problematic. If the spatial position is shown, it is possible to determine whether breathing has leaked and the diaphragm has moved, whether the entire body has been shaken by the body movement, or whether it is shaking in the vicinity of the external thorax.

Furthermore, even if the arrhythmia is severe, it is desirable to display a warning because re-imaging may be necessary. For example, it is assumed that at least three heartbeats are observed in the case of imaging for 6 seconds, but if the waveforms of the heartbeats are largely different due to arrhythmia, it is difficult to remove noise, and it becomes difficult to calculate a stable blood flow characteristic amount. In the determination of the arrhythmia, the frequency component peak is specified as the cardiac cycle in the range of 0.5 to 5 Hz based on the time waveform of the concentration of the ROI placed on the heart or the like, and it is determined whether the specified cardiac cycle peak has a height twice or more as high as the nearby frequency component peak. In the warning display, it is preferable to display the spatial position of the measured cardiac ROI together with the waveform, the cardiac cycle peak frequency, and the like. Because cardiac ROI may be inappropriate, it is desirable for the radiology technician to be able to modify and recalculate the ROI.

When the determination result indicating that the imaging is OK is input by the predetermined operation of the operation unit 23 (step S7; YES), information such as the identification ID for identifying the dynamic image, the patient information, the examination information, the radiation irradiation condition, the image reading condition, the number (frame number) indicating the imaging order, and the like are attached to each frame image of the series of frame images acquired by the dynamic imaging (for example, written in the header area of the image data in DICOM format), and the above is transmitted to the diagnostic console 3 via the communication unit 25 (step S8). Then, the process ends. On the other hand, when the determination result indicating the imaging NG is input by the predetermined operation of the operation unit 23 (step S7; NO), the series of frame images stored in the storage 22 is deleted (step S9), and the process ends. In this case, re-imaging is necessary.

(Operation of the Diagnostic Console 3)

Next, operation of the diagnostic console 3 will be described.

Figure 3:
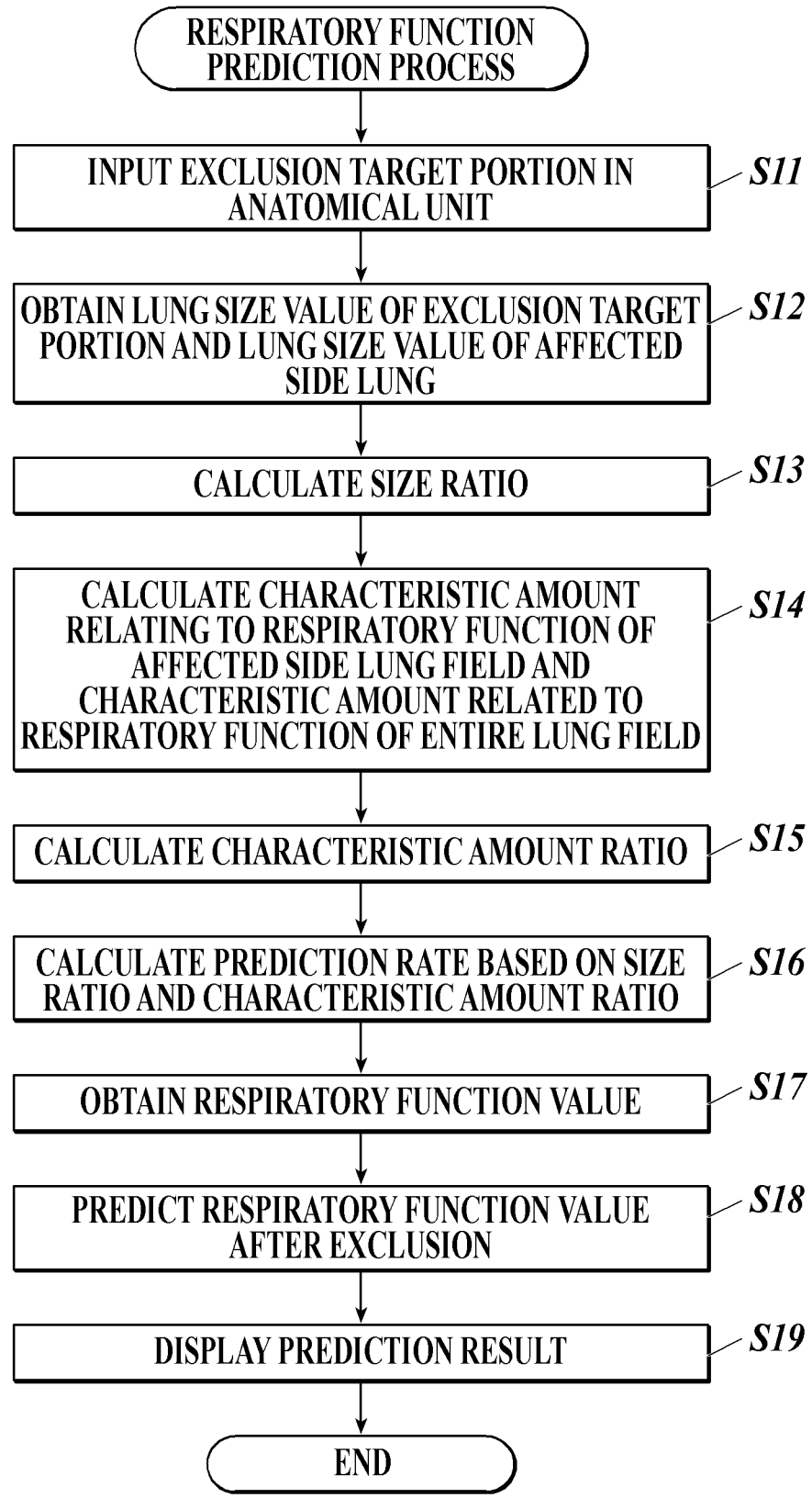
FIG. 3 is a flowchart showing a respiratory function prediction process executed by the controller of the diagnostic console shown in FIG. 1 according to the first embodiment.

In the diagnostic console 3, when a series of frame images of chest dynamic images is received from the imaging console 2 via the communication unit 35, the respiratory function prediction process shown in FIG. 3 is executed by the controller 31 in coordination with the program stored in the storage 32. The respiratory function prediction process is a process of predicting the respiratory function after the pulmonary resection operation. Hereinafter, with reference to FIG. 3, the respiratory function prediction process will be described.

First, an exclusion target portion to be excluded from the lung field by the pulmonary resection operation is input in anatomical units (step S11).

A partial resection of the lung is performed in the anatomical unit that constitutes the lung. The anatomical units constituting the lungs are divided into right and left, lung lobes, lung regions, lung sub-regions, and the like, the above order according to an order from a large size to a small size. FIG. 4 is a diagram showing anatomical units (left and right lungs, lung lobes (right upper lobe, right middle lobe, right lower lobe . . . ), and lung regions (S1+2, 3, 4 . . . )) constituting the lungs. The lung sub-region is a finer section than the lung region.

Generally, a partial resection of the lung is performed in a unit of a lung lobe. Therefore, in step S11, for example, as shown in FIG. 5A, a list of lung lobes is displayed on the display 34, and when a lung lobe is selected by the operation of the operation unit 33 of the user, the selected lung lobe is input as an anatomical unit of the exclusion target portion. In operation, a plurality of lobes may be resected, or the second or subsequent resection may be performed, so that a plurality of lobes may be selected as an exclusion target portion in the check box format as shown in FIG. 5B. If reduction operation is required, resection may be performed on a lung region or lung sub-region unit. Therefore, as shown in FIG. 5C, for example, anatomical units (right lung, left lung, lung lobe, lung region, lung sub-region, etc.) constituting the lung may be displayed in a list on the display 34, and the anatomical unit selected by the mouse or the like of the operation unit 33 may be input as an anatomical unit of the exclusion target portion.

Alternatively, the user may input the anatomical unit of the exclusion target portion using a keyboard or the like of the operation unit 33.

In addition, when the information of the anatomical unit corresponding to the exclusion target portion of the lung field of the subject M is requested to the electronic medical record system via the communication unit 35, and the information of the anatomical unit corresponding to the exclusion target portion of the lung field of the subject M is acquired from the electronic medical record system, the processing in and after step S12 may be performed using the acquired information of the anatomical unit.

Next, based on the input anatomical unit, the lung field of the affected side is specified, and the lung size value of the exclusion target portion and the lung size value of the affected side are obtained (step S12).

The affected side is the lung of the right and left lungs that has the disease, that is, that has the exclusion target portion.

The lung size value is a value representing a size occupied in the entire lung field (for example, a value capable of specifying a ratio (%) of the lung field to the volume of the entire lung field).

In step S12, for example, the lung size value table 321 shown in FIG. 6 is referred to, and the lung size value corresponding to the anatomical unit of the exclusion target portion is acquired. In FIG. 6, the lung size values are expressed based on the number of lung regions counting the number of lung regions for the whole lung as 19, which is shown in the guidelines of the Japanese Society of Lung Cancer. The 19 regions presented in this guideline are counted by counting the upper left leaf "S1+2" and "S3" in the 18 lung regions shown in FIG. 4 as three regions (number of lung regions is 3). The size of the lungs indicated by the number of lung regions being 1 is approximately 1/19 considering the entire lungs as 1. Each lobe and the right and left lungs consist of a plurality of lung regions. That is, the number of lung regions included in the right and left lungs and each lung lobe can specify the lung size value of the lung (either right or left) or the lung lobe (the ratio (%) to the volume of the whole lung) at the exclusion target portion of the anatomical unit.

In FIG. 6, the number of lung regions of each anatomical unit is shown as the lung size value with the number of lung regions of the whole lung being 19 as shown in the guideline of the Japan Lung Cancer Society, but the lung size value is not limited to the number of lung regions shown in the above guideline, and other values may be used as long as the accuracy is high (for example, a value capable of specifying the ratio (%) of the lung to the volume of the lung field as a whole) as a value representing the size occupied in the lung field as a whole. For example, the lung size value of each anatomical unit may be defined by the number of regions of the lung region being 22 regions for the entire lung, or the number of lung sub-regions may be the lung size value.

Next, the ratio (Equation 1) of the lung size value of the exclusion target portion and the lung size value of the lung on the affected side is calculated as the size ratio (step S13).

Size ratio=Pulmonary size value of the exclusion target portion/Pulmonary size value of the affected lung     (Equation 1)

Next, the characteristic amounts relating to the respiratory function of the affected lung field and the entire lung field are calculated (step S14).

The characteristic amount related to the respiratory function of the affected lung field is the characteristic amount related to the respiratory function of the right lung if the affected side is the right lung, and the characteristic amount related to the respiratory function of the left lung if the affected side is the left lung. The characteristic amount related to the respiratory function of the entire lung field is the sum of the characteristic amount related to the respiratory function of the right lung and the characteristic amount related to the respiratory function of the left lung.

As the characteristic amount relating to the respiratory function, for example, a blood flow characteristic amount, a ventilation characteristic amount, or a characteristic amount based on both of them (referred to as a VQ characteristic amount) can be used. Generally, since the blood flow is decreased at the lung point where the ventilation function is decreased, the current respiratory distribution state can be grasped using either the blood flow characteristic amount or the ventilation characteristic amount. However, blood flow may still remain in areas where ventilation function is decreased, such as immediately after a ventilation disorder has occurred. In addition, although there is a ventilation function, there is a place in which there is no blood flow function due to pulmonary embolism or the like. Without both ventilation and blood flow, the respiratory function cannot be ensured. Therefore, by using the VQ characteristic amount based on both the ventilation and the blood flow instead of using the ventilation characteristic amount and the blood flow characteristic amount alone, it is possible to predict the respiratory function after the operation more accurately.

<Blood Flow Characteristic Amount>

The blood flow characteristic amount can be calculated by, for example, the following procedures (1) to (8).

(1) First, a frame image in a breath-holding state is acquired from a series of frame images of the received dynamic image.

For example, for each of a series of frame images, an average pixel value of the entire image is calculated, and when a predetermined number or more of frame images in which an absolute value of a difference value of the average pixel values between an adjacent frame image does not exceed a predetermined threshold value are consecutive, the section is acquired as a frame image in a breath-holding state.

The frame image to be acquired may be any of the resting expiratory position, the resting inspiratory position, the deep breathing expiratory position, or the deep breathing inspiratory position, or may be any of the standing position, the decubitus position, or the sitting position.

(2) A lung field region (right lung field region and left lung field region) is automatically extracted from each acquired frame image, and a measurement target region is set in the extracted lung field region. The measurement target region is a region obtained by excluding a region including a signal unnecessary for calculating a characteristic amount such as noise from the lung field region.

First, a lung field region is extracted from each acquired frame image. The lung field region may be extracted by any method. For example, a threshold value is obtained from a histogram of pixel values (density values) of pixels of a frame image by discrimination analysis, and a region having a signal higher than the threshold value is primary extracted as a lung field region candidate. Next, edge detection is performed in the vicinity of the boundary of the primary extracted lung field region candidate, and the boundary of the lung field region (right lung field region and left lung field region) can be extracted by extracting along the boundary the point where the edge is maximized in the small block in the vicinity of the boundary. FIG. 7 shows an example of an automatically extracted lung field region (right lung field region R, left lung field region L).

Here, the lung parenchyma also exists in the region overlapping with the mediastinum and the diaphragm three-dimensionally, but the lung field region is desirably set to a range excluding the region overlapping with the mediastinum and the diaphragm because the noise in the case where the diaphragm moves by pulsation is large. The heart and the aorta are also desirably excluded from the region because there are many blood flow signals other than the pulmonary blood flow.

Next, a measurement target region is set.

Here, the extracted lung field region may be used as the measurement target region as is, but it is preferable to set the measurement target region excluding a region having a large amount of noise or the like among the lung field regions.

For example, when the blocking process is performed in the subsequent stage, it is desirable to exclude the distance corresponding to half of the block size inside the margin of the extracted lung field region (5.0 mm in the case of a block size of 10 mm) from the measurement target region because the distance includes the signal component outside the lung field. The blood flow characteristic amount may be calculated without performing the blocking process, and in this case, the above becomes unnecessary, and a measurement target region can be set widely up to the lung field margin and used for calculation of the characteristic amount.

In addition, since the outer rib cage margin is subject to a large amount of noise even with a small amount of body motion, it is desirable to exclude this portion from the measurement target region because of poor S/N. In addition, when the blood flow characteristic amount is calculated, since the blood flow rate that changes with the heart rate is small in the lung field peripheral, even if the above is excluded, the influence is small. The exclusion range may be, for example, a fixed range of 1 cm or the like in the horizontal direction (x direction) from the margin of the lung field region. Instead of the fixed range, the exclusion range may be determined by image analysis. For example, since the more the pixel value change in the x-direction (left-right direction) of the image is, the more likely the noise is to be caused by the body motion. Therefore, the pixel value profile in the x-direction may be taken, the slope of the profile may be confirmed from the outer rib cage margin toward the inside direction of the lung field, the portion where the slope is equal to or less than a predetermined threshold may be detected, and the range between the outer rib cage margin and the portion where the slope of the profile is equal to or less than a predetermined threshold may be defined as the range where the body motion noise is likely to be caused. This range can be excluded.

When calculating the blood flow characteristic amount, only the hilar region may be set as the measurement target region, as indicated by R1 and L1 in FIG. 7, among the extracted lung field regions (right lung field region and left lung field region). The hilum is located at the approximate center of the inside of the lung, where bronchi, pulmonary arteries, pulmonary veins, etc. enter and exit the lung. That is, the hilum is the starting position of the blood vessels running in the lung field, the blood flow is high, and the pulmonary blood vessels extend from the hilum toward the outer contour of the lung field.

In order to extract the hilar region, for example, a pulmonary vascular region having a diameter of 1 cm or more in the lung field region may be extracted, and by using a line detection filter targeting 1 cm or more, the hilar region can be extracted.

The frame image to which the outline of the lung field region or the measurement target region automatically extracted by the above-described method is added may be displayed on the display 34, and the user may manually modify the lung field region or the measurement target region using the operation unit 33.

(3) Blocking processing, logarithmic conversion, and the like are performed on the measurement target region of each frame image.

Blocking is a process of replacing the pixel value of each pixel with a representative value (average value, etc.) of the pixel value of a small peripheral block (10 mm rectangle, etc.) including the pixel, and white noise and motion influence can be reduced. In addition, the logarithmic conversion makes it possible to measure the change in the thickness of the substance over time.

Though it is desirable to perform these processes, they may be omitted.

(4) For each pixel of the measurement target region, a waveform of a temporal change of the pixel value is acquired, and a high-pass filter (e.g. 0.8 Hz) or a band-pass filter (cardiac cycle) is applied in the temporal direction.

This makes it possible to reduce the influence of the motion or the like due to the body movement.

The noise removal is not limited to the frequency filter. For example, the high-frequency noise may be removed by smoothing the pixel value in a simple time direction, or the offset may be subtracted from the pixel value by using the average value of the pixel values in the cardiac cycle as the offset. The noise may be removed by polynomial approximation of the waveform of the temporal change of the pixel value.

(5) A frame image corresponding to the end diastole of the ventricle of the heart is set as a reference frame image.

Specifically, a region of interest ROI is set in the ventricular region of the heart of each frame image, and a frame image in which the density value (pixel value) of the region of interest ROI is minimum is set as a reference frame image.

Here, the minimum concentration value unit that the volume of blood in the ventricular region defined as the region of interest ROI is the maximum.

Figure 8:
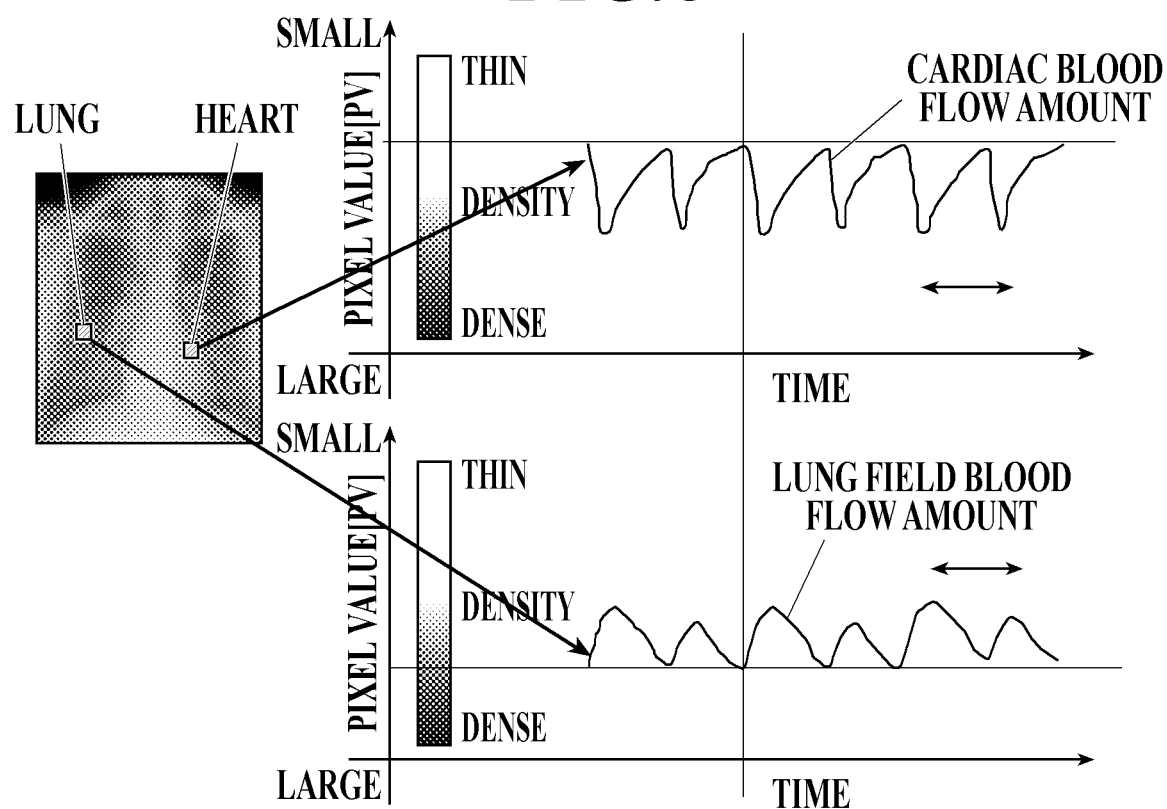
FIG. 8 is a graph showing the increase or decrease of the blood flow rate of the heart on the upper side and the increase or decrease of the blood flow rate of the lung field on the lower side.

FIG. 8 is a graph showing the increase and decrease of the blood flow of the heart on the upper side and the increase and decrease of the blood flow of the lung field on the lower side. In FIG. 8, pixel values are taken on the vertical axis of each graph, and are displayed together with density gradation.

When blood flows into an organ, the transmission of radiation is obstructed by the blood flow, so that the amount of radiation transmission in the radiation image decreases, the pixel value decreases, and the organ appears whitish (i.e., has a low density) on the radiation image. When this is viewed from the relationship between the flow of cardiac blood flowing into and out of the heart and the flow of pulmonary blood flowing into and out of the lung field, as shown in FIG. 8, when the heart is in a ventricular diastolic phase and a large amount of blood flows into the heart, the transmission of radiation is obstructed in the cardiac portion, so that the pixel value is small and the heart appears relatively whitish (at a thin density) on the radiographic image. On the other hand, at this timing, the blood flow flowing into the lung field is small, the amount of transmission of the radiation is large in the lung field portion, so that the pixel value is large, and the lung appears relatively darker (with a dense density) on the radiation image. Conversely, when the heart is in a ventricular systole phase and the blood flow is flowing out of the heart, the amount of transmission of radiation increases in the heart portion, so that the pixel value increases, and the heart appears relatively dark (dense density) on the radiographic image. On the other hand, at this timing, since a large amount of blood flows from the heart into the lung field, the transmission of radiation is obstructed in the lung field portion, so that the pixel value is small and the lung appears relatively whitish (at a low density) on the radiation image.

(6) For each frame image, for each pixel of the measurement target region, a difference value (the amount of change in density from the reference frame image) of the pixel value with respect to the corresponding pixel (the pixel having the same position) of the reference frame image is obtained. This is the blood flow characteristic amount of each pixel.

(7) In each frame image, all the blood flow characteristic amounts of the pixels in the measurement target region calculated in (6) are integrated to obtain the blood flow characteristic amount of the entire lung field. Further, the blood flow characteristic amount of each pixel in the measurement target region in the right lung is integrated to obtain the blood flow characteristic amount of the right lung. Further, the blood flow characteristic amount of each pixel in the measurement target region in the left lung is integrated to obtain the blood flow characteristic amount of the left lung.

(8) The frame image in which the blood flow characteristic amount of the entire lung field is the largest is set as the representative frame image, and the blood flow characteristic amount of the representative frame image is set as the characteristic amount relating to the respiratory function.

The frame image having the largest blood flow characteristic amount of the entire lung field is a frame image having the strongest blood flow characteristic amount appearing in the lung field region and high S/N, and is therefore highly suitable as a representative frame. Note that the characteristic amount relating to the respiratory function is not limited to the blood flow characteristic amount of the representative frame image, and may be a sum value of the blood flow characteristic amounts in a plurality of frame images such as one heartbeat, or may be another method.

<Ventilation Characteristic Amount>

The ventilation characteristic amount can be calculated by the following procedures (1) to (8), for example.

(1) First, a frame image under a breathing state is acquired from a series of frame images of the received dynamic image.

For example, the average pixel value of the entire image is calculated for each of a series of frame images, and an interval in which the amplitude of the waveform representing the temporal change of the average pixel value is equal to or larger than a predetermined threshold value is acquired as a frame image under the breathing state.

The frame image to be acquired may be a resting breath or a deep breath, or may be a standing position, a lying position, or a sitting position.

(2) A lung field region (right lung field region and left lung field region) is automatically extracted from each acquired frame image, and a measurement target region is set.

The lung field region extraction method and the measurement target region setting method are as described above. Since the degree of lung swelling changes for each frame image by the respiration, a known local matching process and warping process (for example, see Japanese Patent Application Laid-Open Publication No. 2012-5729) may be performed to correct the positional deviation of the lung field region between the frame images.

(3) Blocking processing, logarithmic conversion, and the like are performed on the measurement target region from which each frame image is extracted.

Though it is desirable to perform these processes, they may be omitted.

(4) For each pixel in the lung field region, a waveform of the temporal change of the pixel value is acquired, and a low-pass filter (e.g. 0.8 Hz) or the like is applied in the temporal direction.

This can reduce pulsation and white noise effects.

(5) The frame image of the exhalation level is set as the reference frame image.

For example, the position of the diaphragm of each frame image may be automatically extracted by template matching or the like, and a frame image at a timing at which the diaphragm is closest to the apex of the lung may be extracted as a frame image at the exhalation level. It is needless to say that the setting may be performed by other methods.

(6) The frame image of the inspiration level is set as the representative frame image.

For example, the position of the diaphragm of each frame image may be automatically extracted by template matching or the like, and a frame image at a timing at which the diaphragm is farthest from the apex of the lung may be extracted as a frame image at the inspiration position. It is needless to say that the setting may be performed by other methods.

(7) For each pixel of the measurement target region of the representative frame image, a difference value (amount of change in density from the reference frame image) between the pixel value and the corresponding pixel (pixel having the same position) of the reference frame image is obtained. This is the ventilation characteristic amount of each pixel.

In order to enable the moving image display of the ventilation characteristic amount on the respiratory function measurement screen 341 (see FIG. 8), which will be described later, it is preferable that a difference value (amount of change in density from the reference frame image) between the pixel value and the corresponding pixel (pixel having the same position) of the reference frame image is obtained for each pixel of the extracted measurement target region for each frame image.

(8) The ventilation characteristic amounts of the respective pixels in the measurement target region calculated in (7) are all integrated to obtain the ventilation characteristic amount of the entire lung field. In addition, the ventilation characteristic amount of each pixel in the measurement target region in the right lung is integrated to obtain the ventilation characteristic amount of the right lung. In addition, the ventilation characteristic amount of each pixel in the measurement target region in the left lung is integrated to obtain the ventilation characteristic amount of the left lung.

In addition, when the degree of swelling of the lung changes with respiration, the coarse density of the pulmonary blood vessel changes, and therefore, a method of extracting the ventilation characteristic amount by measuring the coarse density of the pulmonary blood vessel may be used. For example, a process of detecting a characteristic point (two or more points) such as a branch point of a pulmonary blood vessel from an image is performed, tracking is performed on each characteristic point by template matching or the like to measure a motion, the distance between the characteristic points of the representative frame image and the amount of change in the distance between the characteristic points of the reference frame image are measured, and this may be used as a ventilation characteristic amount.

<VQ Characteristic Amount>

The VQ characteristic amount can be calculated by, for example, the following procedures (1) to (3).

(1) First, the left-right ratio of each of the ventilation characteristic amount and the blood flow characteristic amount is obtained.

(2) A representative value of the right side value of the left-right ratio of the ventilation characteristic amount and the right side value of the left-right ratio of the blood flow characteristic amount obtained in (1) is obtained and set as VQ'(R). For example, when the left-right ratio (right:left) of the ventilation characteristic amount is 5:5 and the left-right ratio (right:left) of the blood flow characteristic amount is 7:3, since the value on the right side of the ventilation characteristic amount is 5 and the value on the right side of the blood flow characteristic amount is 7, VQ'(R)=5 if the representative value is the minimum value. This VQ'(R) is defined as the VQ characteristic amount in the right lung. Similarly, for the left lung, the representative value of the left side value of the left-right ratio of the ventilation characteristic amount and the left side value of the left-right ratio of the blood flow characteristic amount obtained in (1) is obtained and set as VQ'(L). This VQ'(L) is defined as the VQ characteristic amount in the left lung.

(3) VQ'(R)+VQ'(L) is the VQ characteristic of the whole lung field.

The representative value may be a minimum value, or may be a maximum value, an average value, or a median value. Alternatively, the representative value may be a value obtained by adding the value on the right side of the left-right ratio of the ventilation characteristic amount and the value on the right side of the blood flow characteristic amount, or may be a multiplied value. The use of a minimum value is preferred because it allows the characteristic amount with the lower function between ventilation and blood flow to be reflected in the predictive rate.

When the calculation of the characteristic amount is completed, the ratio of the characteristic amount relating to the respiratory function of the affected lung field and the entire lung field is calculated as the characteristic amount ratio (step S15). This characteristic amount ratio is the contribution rate of the affected lung to the entire breath.

Next, based on the calculated size ratio and characteristic amount ratio, a prediction rate for predicting the respiratory function value when the exclusion target portion is excluded from the entire lung field is calculated (step S16).

The prediction rate can be obtained by the following equation (2).

$$\text{Prediction Rate} = 1 - \text{Characteristic amount Ratio} \times \text{Size Ratio} \quad \text{(Equation 2)}$$

The blood flow characteristic amount, the ventilation characteristic amount, and the VQ characteristic amount described above are examples of characteristic amounts relating to the respiratory function, and may be obtained by another method.

Next, in step S17, the respiratory function value of the subject is acquired.

As the respiration function value, for example, a measurement value measured by a spirometry test is acquired as the respiration function value. The guidelines of the Japan Lung Cancer Society include % FEV1 as the respiratory function value used to calculate the risks of lung cancer operations, but other respiratory function values may be obtained. For example, it may be FEV1, VC, % VC, FVC, % FVC, FEV1%, % FEV1%.

The respiratory function value may be estimated from the dynamic image or the still image. For example, the difference between the lung field area of the frame image of the deep breathing exhalation position (maximum exhalation position) and the lung field area of the frame image of the deep breathing inhalation position (maximum inhalation position) can be used to estimate the ventilation volume. The image at this time may be a front image or a side image, and the accuracy is improved by calculating the lung field volume using both of them and estimating the ventilation volume from the lung field volume. In addition, the difference between the lung field areas of the frame image of the exhaled air level and the frame image of the inspired air level at the time of resting respiration, deep breathing, or forced breathing may of course be calculated, or the difference between the lung field areas for one second may be used to calculate the ventilation amount in the same manner as FEV1.

In the case of a still image, it is only necessary to use an image taken only at the expiratory position or the inspiratory position, or if FEV1, the ventilation amount may be estimated similarly using an image taken at the inspiratory position and 1 second after the expiration starts. Alternatively, the entire lung field may not be used, and the ventilation volume may be estimated from the diaphragm motion volume.

In the measurement of the respiratory function value, since the patient load is high in the spirometry examination, the patient load can be reduced by measuring the respiratory function value from the dynamic image, and the examination can also be simplified.

Next, based on the prediction rate calculated in step S16, the post-operative respiration function value (the respiratory function value after the exclusion target portion is excluded from the lung field) is predicted (step S18).

Postoperative respiratory function values can be predicted by the following equation (3).

Postoperative Respiratory Function Value=Respiratory Function Value×Prediction Rate   (Equation 3)

Next, the predicted post-operative respiration function value is displayed on the display 34 (step S19), and the respiratory function value prediction process ends.

The relationship of the order from step S11 to step S19 of the respiratory function prediction process is not limited to the one described above. For example, step S17 may be performed before step S11, or steps S12 and S13 and steps S14 and S15 may also be interchanged. In addition, the order may be changed as appropriate.

Figure 9:
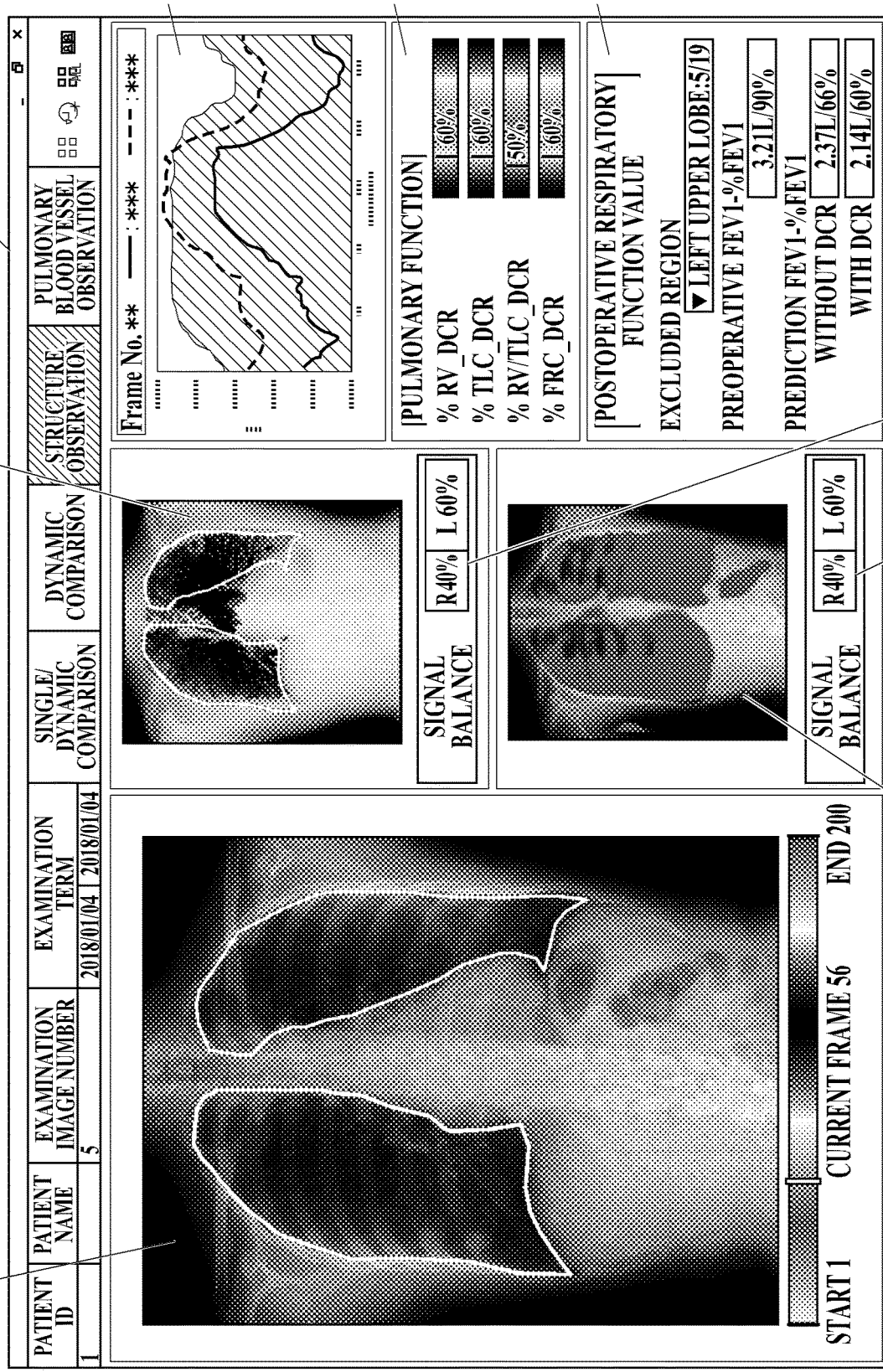
FIG. 9 is a diagram showing an example of a respiratory function measurement screen.

In step S19, it is preferable not only to display the predicted respiratory function value after the operation, but also to display the dynamic image, the blood flow characteristic amount, the ventilation characteristic amount, and the like used for the prediction as in the respiratory function measurement screen 341 shown in FIG. 9, for example.

Hereinafter, a respiratory function measurement screen 341 as an example of a screen displayed on the display 34 in step S19 will be described with reference to FIG. 9. The display control of the respiratory function measurement screen 341 is executed by the controller 31 in coordination with the program stored in the storage 32.

The respiratory function measurement screen 341 includes a dynamic image display column 341a, a blood flow characteristic amount display column 341b, a blood flow left-right ratio display column 341c, a ventilation characteristic amount display column 341d, a ventilation left-right ratio display column 341e, a graph display column 341f, a lung function estimated value display column 341g, a prediction result display column 341h, and the like.

In the dynamic image display column 341a, a dynamic image composed of a frame image imaged in a breathing state among a series of dynamic images transmitted from the imaging console 2 is displayed. By default, for example, the image may be repeatedly reproduced sequentially from the first frame image to be reproduced as a moving image. Various displays of moving images and still images can be performed, such as playback/pause by clicking a moving image, or changing a display frame using a mouse wheel or a scroll bar. By displaying the dynamic image during respiration taken at the same time as the prediction of the respiration function value, it is possible to confirm whether or not there is an abnormality by confirming the motion of the lung field together with the predicted value of the respiration function value after the operation. In the preoperative judgment, it is necessary to make a comprehensive physician judgment considering not only data of the predicted value of the respiratory function value after the operation but also various information. Therefore, it is useful to display a moving image that captures the motion of the entire chest to understand the adhesions and infiltration of the lungs, the hardness of the tumor, the positional relationship in the depth direction with other structures, and the like, which cannot be understood by the still image alone.

In the blood flow characteristic amount display column 341b, the calculated blood flow characteristic amount is displayed when the blood flow characteristic amount is calculated as the characteristic amount related to respiration in step S14.

Figure 10:
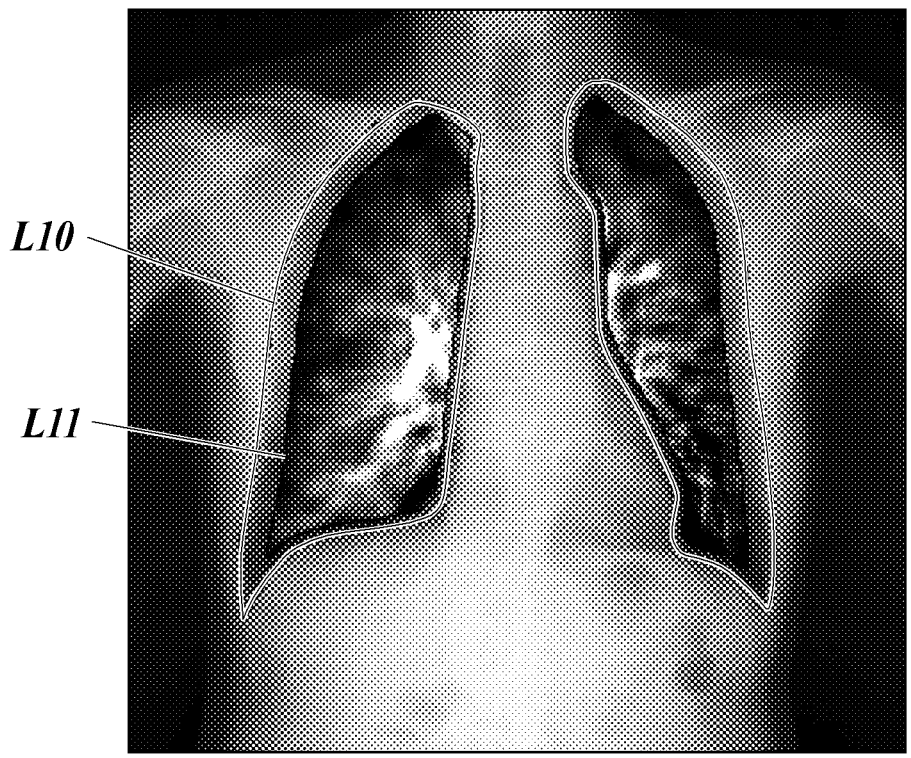
FIG. 10 is a diagram showing an example of a blood flow characteristic amount image displayed in the blood flow characteristic amount display column of the respiration function measurement screen.

For example, as shown in FIG. 10, each pixel of the measurement target region of the representative frame image to which a color corresponding to the value of the blood flow characteristic amount is added (referred to as a blood flow characteristic amount image) is displayed in the blood flow characteristic amount display column 341b. In FIG. 10, the color of each pixel of the representative frame image may be rewritten to a color corresponding to the blood flow characteristic amount, or may be displayed transparently.

As described above, when calculating the blood flow characteristic amount, the area within a predetermined distance from the inner side of the margin of the automatically extracted lung field region is excluded from the measurement target region. Since there is a possibility that an artifact occurs in the region between the automatically extracted lung field region and the measurement target region, it is preferable to display the blood flow characteristic amount only in the measurement target region in the blood flow characteristic amount image so that the artifact is not confused by a user such as a doctor.

However, if the blood flow characteristic amount is not displayed in the region between the automatically extracted lung field region and the measurement target region, there is a possibility that the physician feels uncomfortable, and therefore, the region between both regions may be filled with the blood flow characteristic amount in the neighboring measurement target region and displayed.

In the blood flow characteristic amount image, as shown in FIG. 10, it is preferable that the lung field margin line L10 indicating the contour of the automatically extracted lung field region and the measurement target contour line L11 indicating the contour of the measurement target region are also displayed in a form overlaid on the representative frame image. Further, it is desirable that the lung field margin line L10 and the measurement target contour line L11 are displayed not only in the representative frame image but also in the ventricular end-diastolic frame image. Since the lung parenchyma is also present in a region overlapping with the longitudinal contour or the diaphragm in three dimensions, it is desirable to be able to correct the lung field region and the measurement target region by correcting the lung field margin line L10 according to the request of the physician. Since the cardiac region is the largest in the end diastole of the ventricle, the lung field margin line L10 is modified with reference to the frame image in the end diastole of the ventricle, so that the heart wall can be prevented from entering and leaving the lung field region and the measurement target region.

For example, when the lung field margin line L10 is dragged and dropped by the operation unit 33, the lung field margin line L10 may be rewritten in accordance with the operation, or when a new lung field margin line is added in a necessary point by the operation of the operation unit 33, the lung field margin line closest to the added lung field margin line may be replaced with the added lung field margin line, or any other method may be used. When the lung field margin line L10 is corrected, it is desirable to not display the color indicating the blood flow characteristic amount and to improve the visibility of the representative frame image.

When the lung field margin line L10 is rewritten, the contour of the measurement target region is corrected to be a predetermined distance from the inside of the new lung field margin, and the blood flow characteristic amount, the ratio of the left and right blood flow characteristic amounts displayed in the blood flow left-right ratio display column 341c, the predicted respiratory function value after the operation, and the like are recalculated (corrected) based on the corrected measurement target region, and the display is also updated.

On the other hand, for a physician who conducts clinical research, a blood flow characteristic amount display column 341b may be configured to switch and display a blood flow characteristic amount image in which only a color corresponding to the blood flow characteristic amount is added to each pixel without a representative frame image in the background, or may be configured to display a blood flow characteristic amount image in which the blood flow characteristic amount is calculated and the corresponding color is added to the outside of the lung field region transparent from the representative frame image. By doing so, it is possible for the user to grasp the presence or absence of abnormality in the blood flow outside the lung field and blood flow conditions such as the heart and the aorta. In addition, the measurement target region may be corrected by the operation of the measurement target contour line L11 on the operation unit 33 (for example, by the above-described dragging and dropping, writing, or the like). In this case, the blood flow characteristic amount, the ratio of the left and right blood flow characteristic amounts displayed in the blood flow left-right ratio display column 341c, the postoperative respiratory function predicted value, and the like are recalculated based on the corrected measurement target region, and the display is also updated. Further, the lung field region may be calculated and corrected backward from the corrected measurement target region, and the lung field margin line L10 displayed in the blood flow characteristic amount display column 341b may be updated.

As a reference, the upper end and lower end of the lung field region of the representative frame image may be detected, the left and right lung field regions may be divided into three equal parts in the upper, middle and lower part to create six divided lung field regions, and the ratio of the integrated value of the blood flow characteristic amount in each of the six divided regions to the integrated value of the blood flow characteristic amount in the entire lung field may be calculated and shown. The ratio of each of the right and left lungs as a whole may be calculated and displayed. This makes it possible to grasp to some extent whether or not the blood flow distribution in the upper, middle, and lower lung fields is normal, although the anatomical correspondence is inaccurate. In addition, the ratio of the area of the measurement target region in each of the six divided regions to the area of the measurement target region of the entire lung field, the average value of the blood flow characteristic amount, and the like may be displayed. The division is not limited to three equal portions, but may be two equal portions in the vertical direction or the like.

In this manner, by displaying the automatically extracted lung field region and the measurement target region serving as the calculation target of the blood flow characteristic amount on the display 34, the user can confirm which region the respiratory function prediction performed is based on. In addition, by allowing the contour of the lung field region and the measurement target region to be modified in accordance with the user's operation, it is possible to predict the respiratory function based on an appropriate region.

Figure 11:
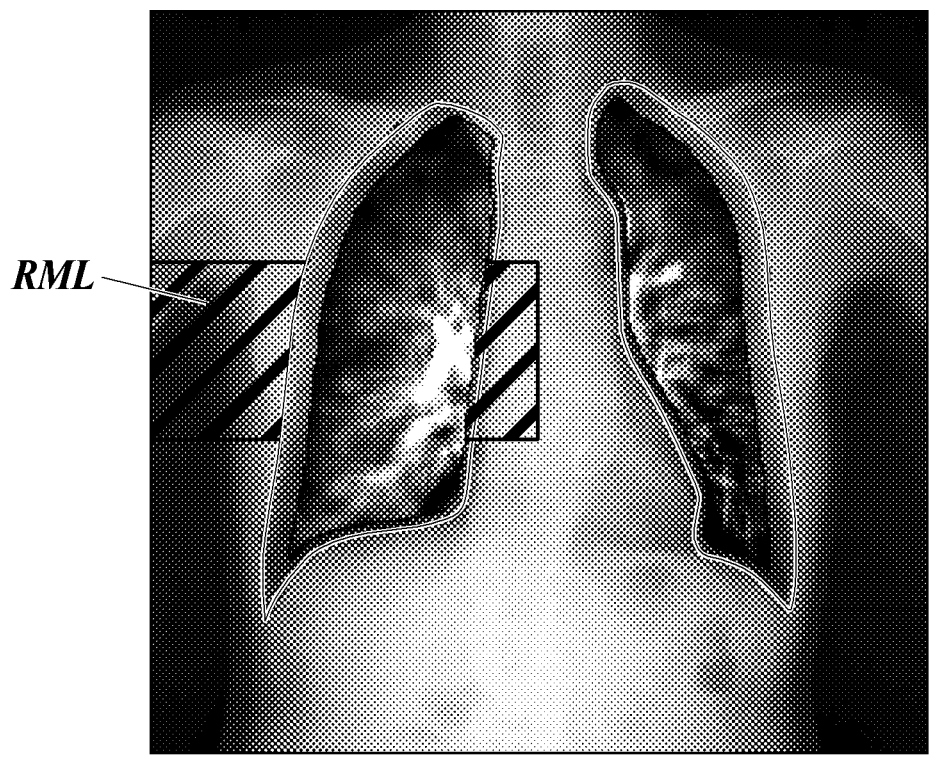
FIG. 11 is a diagram showing an example of an image in which the exclusion target portion is highlighted.

In addition, when displaying the blood flow characteristic amount image in the blood flow characteristic amount display column 341b, it is desirable to highlight the range corresponding to the exclusion target portion so that the correspondence of the position with the exclusion target portion can be easily understood. For example, if the right middle lobe (RML) is to be excluded, the exclusion target portion is highlighted by surrounding the portion as shown in FIG. 11. In order to prevent not being able to understand an accurate positional relationship and to prevent misunderstanding the portion with the measurement target region of the blood flow characteristic amount, it is desirable to highlight only the region without the blood flow characteristic amount as shown in FIG. 11. The name (right middle lobe, RML) of the exclusion target portion should also be displayed in characters.

Figure 12:
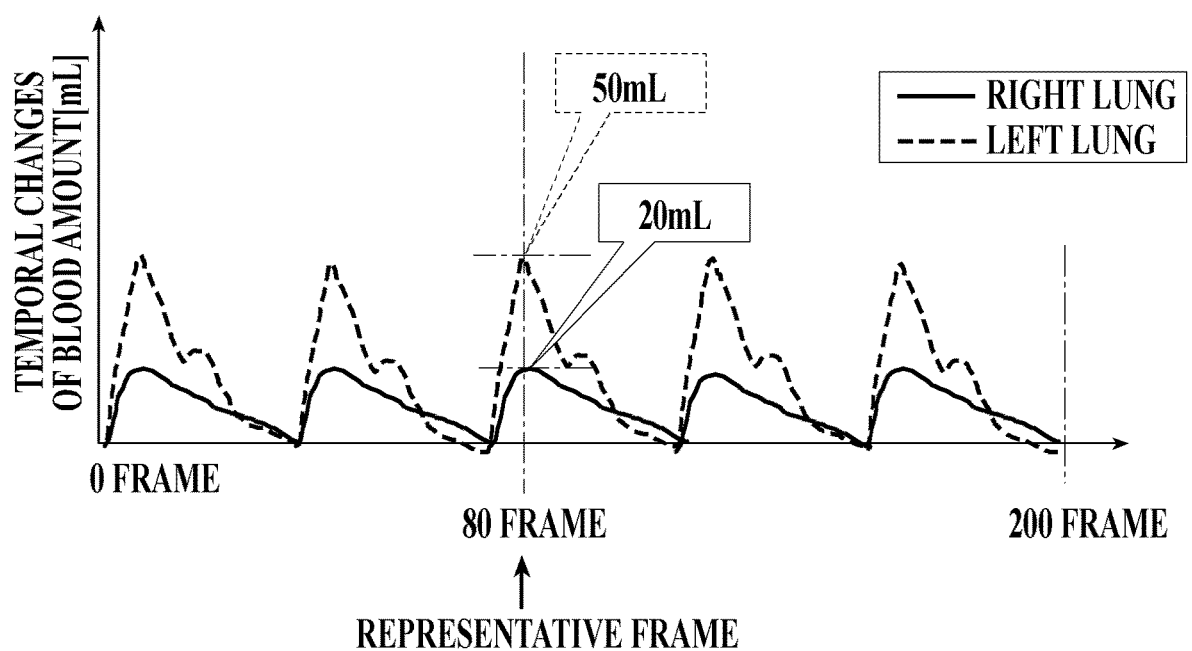
FIG. 12 is a diagram showing an example of a detailed analysis of the blood flow characteristic amount image.

In addition, for example, a detailed button may be provided in the blood flow characteristic amount display column 341b, a detailed analysis screen (not shown) may be displayed when the detailed button is pressed, and a detailed analysis of the ROI (region of interest) set on the blood flow characteristic amount image may be performed by the operation unit 33 to display the analysis result. For example, as shown in FIG. 12, waveforms indicating temporal changes of blood amount [mL] for each ROI obtained by analyzing the blood flow characteristic amount image may be displayed (in FIG. 12, the left lung and the right lung are denoted as ROIs, respectively).

The temporal change of the blood in the ROI can be obtained as follows.

In each pixel, if there is no change in thickness other than the blood vessel and blood at two different times, the amount of change in thickness of the blood vessel and blood can be obtained from the difference in the logarithm of the pixel values at the two different times, as shown in Equation 4.

$$Xb - Xb' = (\log I - \log I')/(-\mu b \cdot \rho b) \qquad \text{(Equation 4)}$$

The pixel value of each pixel in each frame image is I, and the pixel values of the pixels in the reference frame image is I', the thickness of the blood vessel/blood (blood) of each pixel in each frame image (i.e., the distance at which X-rays pass through the subject) is Xb [cm], and the thickness of the blood vessel/blood (blood) of each pixel in the reference frame image is Xb'. In addition, the mass-absorption coefficients of blood vessels and blood are μb [cm$^2$] and the density of blood vessels and blood is ρb [g/cm$^3$]. μb and ρb may be, for example, μb=0.2 [cm$^2$ per gram], ρb=1.1 [g per cm$^3$], or the like based on the document information. That is, by dividing the pixel value (log I–log I') of each pixel of the blood flow characteristic amount image by (−μb·ρb), the blood vessel/blood thickness change amount Xb-Xb of each pixel can be determined.

The temporal change volume VOL[cm$^3$] (=VOL[mL]) of the blood of each pixel can be obtained by multiplying the blood vessel/blood thickness change volume Xb-Xb' obtained by Equation (4) by the area per pixel (for example, 0.16 [cm$^2$/pix]), and the temporal change of the blood in the ROI can be obtained by summing the VOL obtained for each pixel in the ROI.

In the detailed analysis screen, for example, as shown in FIG. 12, a waveform indicating a temporal change of blood in which the right lung and the left lung are set as ROIs may be displayed as a default on the detailed analysis screen. Further, when displaying a waveform indicating a temporal change of blood, it is preferable to display the position of the representative frame image of the blood flow characteristic amount image on the waveform. Thus, not only can the temporal change of the blood entering and leaving the ROI be confirmed in detail, but also it is possible to confirm which frame image was used to calculate the contribution rate (left-right ratio) of the left and right lungs to the respiratory function. If the relationship between the waveform and the representative frame image is inappropriate, the physician may be able to modify the representative frame image. For example, by allowing the physician to change the representative frame image in a case where the body movement occurs and the measured representative frame image is inappropriate or in a case where an arrhythmia occurs, it is possible to measure the blood flow characteristic amount that is more clinically meaningful. When the representative frame image is modified, the overall calculation of the postoperative respiratory function prediction is updated (recalculated).

Incidentally, in the detailed analysis screen, it may be displayed by calculating a wave that shows the temporal change of the cumulative value and other representative values of the blood flow characteristic amount of each pixel in the ROI (e.g., average value, median value, maximum value, minimum value, etc.).

Further, since the blood flow characteristic amount is calculated for each frame image, a blood flow characteristic amount image may be generated for each frame image. The blood flow characteristic amount image is displayed by, for example, replacing each pixel of the frame image used for calculation of the blood flow characteristic amount with a color corresponding to the blood flow characteristic amount, or superimposing the pixel on the frame image. Then, when the blood flow characteristic amount image displayed in the blood flow characteristic amount display column 341*b* (the blood flow characteristic amount image corresponding to the representative frame image) is clicked on the operation unit 33, the blood flow characteristic amount image may be sequentially displayed in frame order to display a moving image, and after the moving image is reproduced, the blood flow characteristic amount image corresponding to the representative frame image may be displayed again. As a result, it is possible to display a change in the blood flow that cannot be grasped by reproducing the dynamic image itself. It is preferable that ON/OFF of superimposing the blood flow characteristic amounts on the frame images be switched by the operation unit 33.

Note that while the blood flow characteristic amount image is an image imaged in a breath-holding state, a dynamic image imaged under a breathing state displayed in the dynamic image display column 341*a* (referred to as a respiratory dynamic image) changes a respiratory phase when displayed as a dynamic image, and therefore, a frame image having the same or similar respiratory phase to the blood flow characteristic amount image may be extracted from the frame image of the respiratory dynamic image based on the diaphragm position or the like, and the frame image of the respiratory dynamic image may be displayed as a still image as a representative frame image. The respiratory dynamic image may be always reproduced and displayed, and the position of the representative frame image may be displayed in a conspicuous manner on the scroll bar. A button for reproducing a moving image from the representative frame image may be provided. Further, the blood flow characteristic amount image may be displayed by mapping on the still image display of the representative frame image. As a result, spatial positional correspondence between the blood flow characteristic amount image and the breathing image is easy, and comparison in the case where there is an abnormal portion or the like becomes easy.

In the blood flow left-right ratio display column 341*c*, the ratio of the blood flow characteristic amount of the right lung to the blood flow characteristic amount of the entire lung field (the characteristic amount ratio of the right lung (%)) and the ratio of the blood flow characteristic amount of the left lung to the blood flow characteristic amount of the entire lung field (the characteristic amount ratio of the left lung (%)) (the left-right ratio) are displayed. The ratio of the characteristic amount of the right lung indicates the contribution rate to the respiratory function of the right lung, and the ratio of the characteristic amount of the left lung indicates the contribution rate to the respiratory function of the left lung.

Figure 13A:
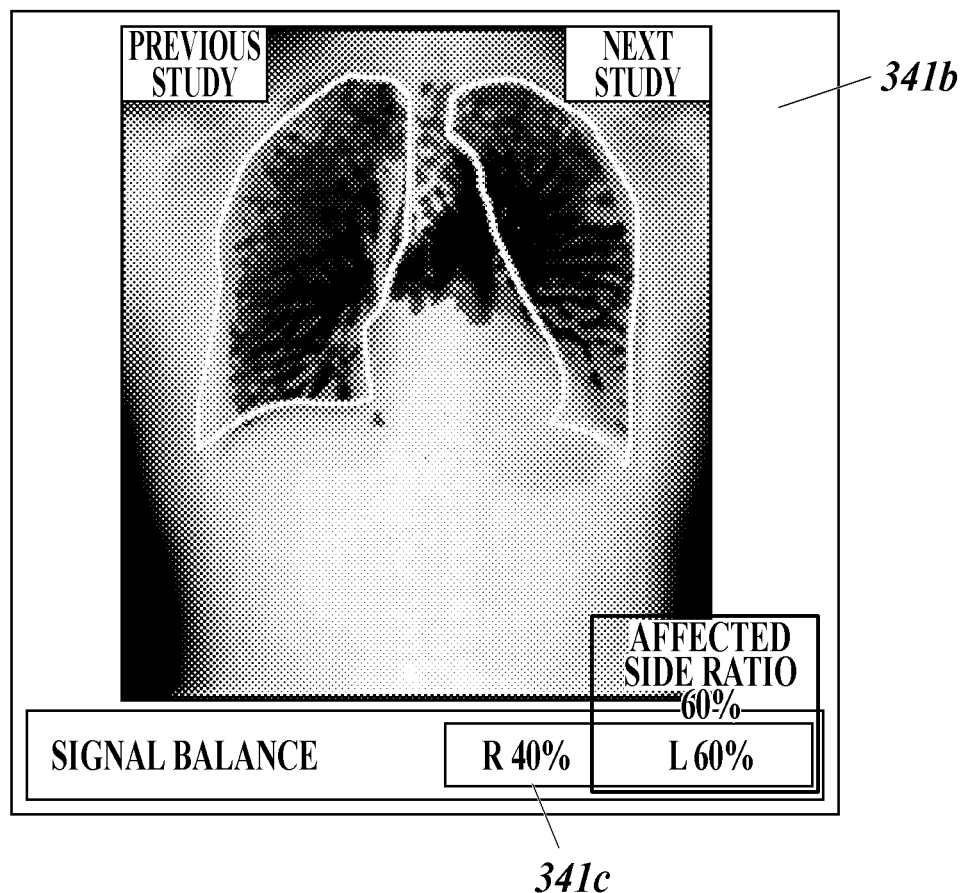
FIG. 13A is a diagram showing an example of displaying a proportion of the left and right in a DCR mode.

Here, as shown in FIG. 13A, the display of the characteristic amount ratio (referred to as the affected side ratio) on the affected side of the left-right ratio may be highlighted. This enables the user to immediately grasp whether the contribution to the respiratory function by the lung on the affected side having the exclusion target portion is larger or smaller than that of the other lung.

Figure 13B:
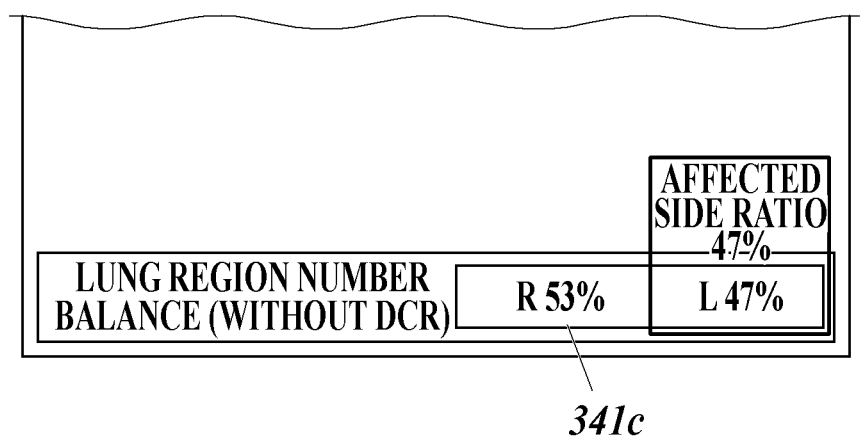
FIG. 13B is a diagram showing an example of displaying a proportion of the left and right in a no DCR mode.

In addition, when the left-right ratio based on the characteristic amount ratio cannot be calculated for some reason, such as a case in which there is the imaging error of the dynamic image or a case in which the blood flow characteristic amount is not calculated as the characteristic amount relating to the respiratory function, it is preferable to be able to operate in the no DCR (Dynamic Chest Radiology) mode (the mode in which the left-right ratio is calculated and the respiratory function value is predicted without the image (without using the characteristic amount ratio (i.e., the contribution rate))). In this case, for example, as shown in FIG. 13B, the blood flow characteristic amount image is not displayed, and it is specified that the mode is the no DCR mode. The left-right ratio is calculated from the number of regions without using the blood flow characteristic amount and displayed. For example, in the case of the number of lung regions counting the number of lung regions of the whole lung as 19, which is shown in the guideline of the Japanese Society of Lung Cancer, the number of lung regions of the right lung and the number of lung regions of the left lung are 10:9, and therefore, the number of lung regions of the right lung and the left lung are displayed as 53% and 47% respectively. Note that a mode in which the left-right ratio is calculated and the respiratory function value is predicted using the characteristic amount of the image is referred to as a DCR-present mode opposed to the no DCR mode.

In the ventilation characteristic amount display column 341d, when the ventilation characteristic amount is calculated as the characteristic amount relating to respiration in step S14, the calculated ventilation characteristic amount is displayed.

Since the display method of the ventilation characteristic amount in the ventilation characteristic amount display column 341d is a method in which the blood flow characteristic amount in the description of the display method of the blood flow characteristic amount in the blood flow characteristic amount display column 341b is replaced with the ventilation characteristic amount, the description will be incorporated.

In the ventilation left-right ratio display column 341e, the ratio (left-right ratio) of the ventilation characteristic amount of the right lung and the ventilation characteristic amount of the left lung is displayed. The display method of the left-right ratio in the ventilation left-right ratio display column 341e is a method in which the blood flow characteristic amount in the description of the display method of the left-right ratio of the blood flow characteristic amount in the blood flow left-right ratio display column 341c is replaced with the ventilation characteristic amount, and therefore, the description will be incorporated.

In the graph display column 341f, a temporal change of a measured value relating to a breathing operation which can be measured by analyzing a dynamic image such as a temporal change of a position of a diaphragm, a temporal change of an estimated lung volume, or the like is calculated and displayed in a graph. As a result, the breathing operation can be instantaneously grasped, and the overall judgment of the respiratory surgical department can be made.

In the lung function estimated value display column 341g, an estimated value of the respiratory function estimated from the dynamic image is displayed. For example, estimates of pulmonary function such as RVs, TLCs, RV/TLC, FRCs, etc. are displayed.

Figure 14:
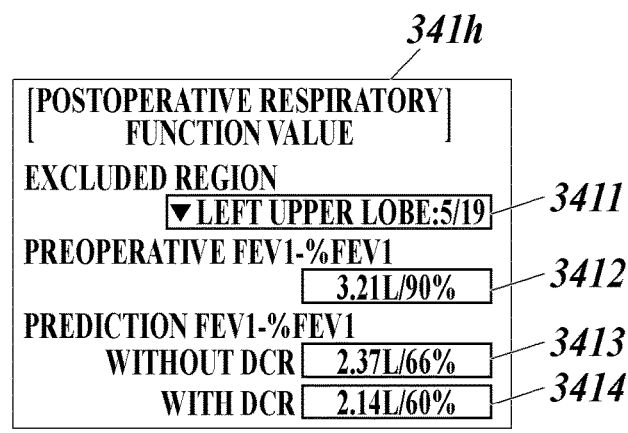
FIG. 14 is a diagram showing an example of a display of the respiratory function predicted value in the respiratory function measurement screen.

In the prediction result display column 341h, the predicted postoperative respiratory function value and the like are displayed. For example, as shown in FIG. 14, information 3411 indicating the lung region of the exclusion target and the percentage of the exclusion target with relation to the entire lung region, information 3412 indicating the preoperative FEV1 and % FEV1, information 3413 indicating the predicted FEV1 and % FEV1 (in the case of the no DCR mode), information 3414 indicating the predicted FEV1 and % FEV1 (in the case of the DCR-present mode), and the like are displayed. Thereby, the user can grasp the predicted value of the postoperative respiratory function value and the change from the preoperative respiratory function value. The prediction result display column 341h may also display the prediction rate.

Figure 15:
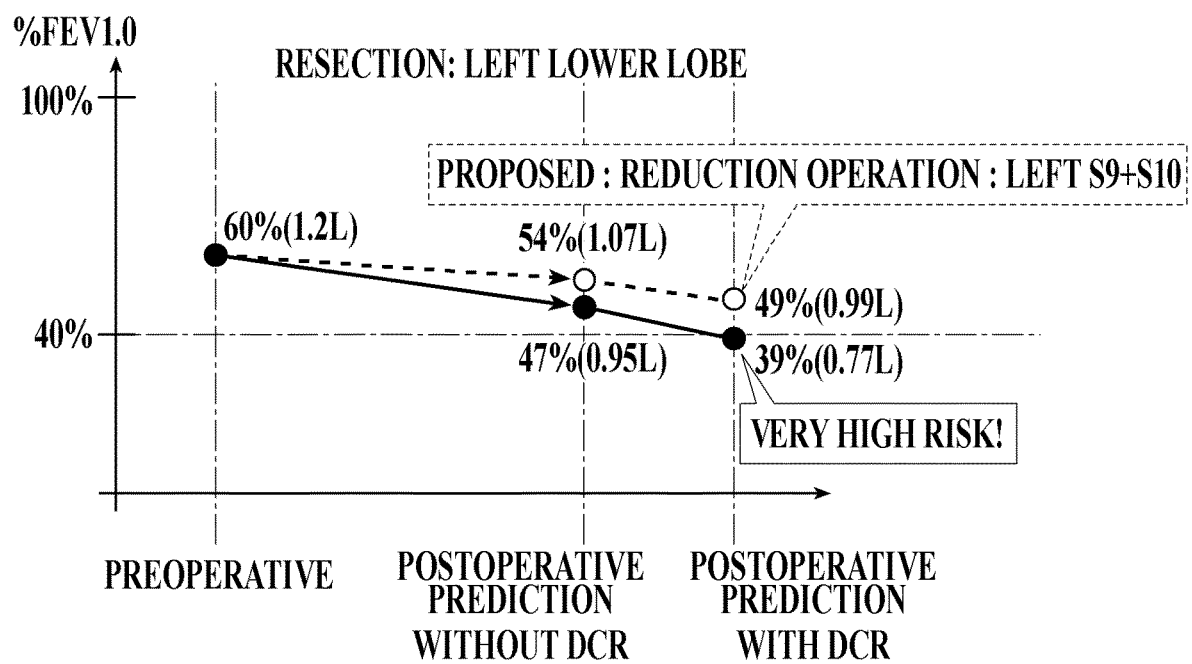
FIG. 15 is a diagram illustrating a display example of a graph arranging a respiration function value before operation and a predicted respiration function value after operation.

As shown in FIG. 15, it is preferable that the respiratory function value before operation and the predicted respiratory function value after operation are displayed aligned in a graph on the display 34. By displaying the graph, the user can immediately visually recognize and understand the comparison between the preoperative and postoperative values and the magnitude of the postoperative respiratory function value (% FEV1 value in FIG. 15).

At this time, it is preferable to calculate and display not only the respiratory function value but also the size (percentage with relation to the entire lung field) of the lung field on the affected side based on the number of lung regions. In addition, as a prediction after the operation, only the respiration function value predicted in the mode with DCR may be displayed, but in order to make the influence due to the contribution rate of the respiration function of the affected side easier to understand, it is preferable to also describe the respiration function value predicted in the mode without DCR (i.e., the respiratory function value predicted by multiplying (1—(the number of lungs regions in the anatomical unit of the exclusion target portion divided by the number of lung regions in the affected side) to the respiration function value obtained in step S17 without considering the contribution rate on the affected side).

When the postoperative risk is within a predetermined risk level range, such as the postoperative prediction result is 40% or less, it is recommended to simulate the case of reduction operation.

In addition, postoperative prediction by pulmonary blood flow scintigraphy may also be described when pulmonary blood flow scintigraphy is performed. The physician can judge the risk comprehensively after arranging all the prediction results. The image of the pulmonary blood flow scintigraphy may also be displayed aligned with, for example, a blood flow characteristic amount image, a ventilation characteristic amount image, or the like. Since the information that can be captured by each modality is different, a more accurate judgment can be made by comparing the two modalities.

When the predicted respiratory function value after operation falls within a range of a predetermined risk level, it is preferable to determine that the patient is in a warning state and display a message to that effect on the display 34. For example, "Very High Risk!" or the like may be displayed beside the display column of the predicted % FEV1 (see FIG. 15). Based on the guidelines of the Japan Lung Cancer Society, when the predicted postoperative % FEV1 is 40% or less, it is basically judged that the state is in a warning status, but other thresholds may be set. For example, if the predicted postoperative % FEV1 is 40% or more, the risks are sufficiently high, and therefore, 50% or less may be used as a near-warning condition and reflected in the display. The judgment of the warning state or the near-warning state is based on the prediction result of the postoperative respiratory function value calculated based on the dynamic image, but the judgment may be made using the prediction result of the respiratory function value by the no DCR mode or the pulmonary blood flow scintigraphy examination.

When the prediction result of the postoperative respiratory function value is the warning state or the near-warning state, the suggestion of the reduction operation may be displayed, and candidates for the exclusion target portion by the reduction operation may be presented (displayed on the display 34).

For example, in the case of the reduction operation of the left lower lobe, since there are four candidates even in the case of the lung region, four candidates are displayed on the display 34, the respiratory function prediction process is executed with the lung region selected by the operation unit 33 as an exclusion target portion, and the predicted value of the respiratory function value in the case of the reduction operation is recalculated (simulated) and displayed.

Conversely, in step S11, an anatomical unit may be input in advance on the assumption of a reduction operation. For example, as shown in FIG. 5C, a screen for inputting the exclusion target portion is used as a user interface capable of selecting a lung region. For example, if there is a lesion in the "S9" region of the lower left lobe, if "Left S9" is selected on the interface shown in FIG. 5C, first, the respiration function prediction process is executed by the controller 31 with the lower left lobe as an exclusion target portion, and when the prediction result is a warning state or a near-warning state, the predicted value of the respiratory function value in the case where the region "S9" of the lower left lobe is set as a resection target place by the reduction operation is calculated (simulated), and the predicted value of the respiratory function value is displayed on the display 34. As a result, it is possible to grasp in advance the lung region which needs to be excluded when proposing the reduction operation, and it is possible to perform postoperative prediction for the exclusion target portion usually on a lobe-by-lobe unit, and immediately perform postoperative prediction for the reduction operation if in the warning state or the like.

The warning display or the reduction operation proposal may be made immediately when the predicted value is issued. For example, if the result of the spirometry examination and the dynamic image have already been input and the exclusion target portion has been newly input, a warning/reduction operation may be proposed on the screen.

As described above, according to the diagnostic console 3, when the exclusion target portion input by the operation unit 33 is input in the anatomical unit, the controller 31 specifies a partial region of the lung field in which the characteristic amount relating to the respiratory function is calculated in the plurality of frame images based on the input anatomical unit, calculates the characteristic amount relating to the respiratory function in the partial region of the lung field specified from the plurality of frame images and the characteristic amount relating to the respiratory function of the entire lung field, and calculates the prediction rate based on the characteristic amount ratio which is the ratio of the calculated two characteristic amounts.

Therefore, when the respiratory function value in the case where the exclusion target portion is excluded from the lung field is predicted using the dynamic image of the chest, the exclusion target portion can be specified easily and accurately.

The controller 31 identifies the lung field region on the side including the exclusion target portion between the left and right side as a partial region of the lung field for calculating the characteristic amount related to the respiratory function based on the input anatomical unit, calculates the characteristic amount ratio, acquires the lung size value of the anatomical unit corresponding to the exclusion target portion and the lung size value of the anatomical unit corresponding to the lung field on the side including the exclusion target portion from the storage 32 in which the lung size value for each anatomical unit configuring the lung is stored in advance, and calculates the prediction ratio based on the value obtained by multiplying the ratio of the lung size value of the anatomical unit corresponding to the obtained exclusion target portion and the lung size value of the anatomical unit corresponding to the lung field including the exclusion target portion by the characteristic amount ratio. Therefore, since the prediction rate can be calculated without specifying the region of the exclusion target portion from the plurality of frame images, it is possible to improve the prediction accuracy of the respiratory function value after the exclusion of the exclusion target portion.

The controller 31 acquires the respiratory function value of the entire lung of the subject, multiplies the acquired respiratory function value by the prediction rate, and predicts the respiratory function value when the exclusion target portion is excluded from the lung field. Therefore, it is possible to predict the respiratory function value when the exclusion target portion is excluded from the lung field.

Since the controller 31 displays the predicted value of the respiratory function value when the exclusion target portion is excluded from the lung field on the display 34, the user can grasp the predicted value of the respiratory function value when the exclusion target portion is excluded from the lung field.

By further displaying the characteristic amount ratio together with the predicted value of the respiratory function value, the user can recognize the contribution rate of the affected side lung field to the respiratory function.

The controller 31 extracts the left and right lung field regions from the plurality of frame images, sets the measurement target regions in the extracted left and right lung field regions, and calculates the characteristic amounts relating to the respiratory function of the partial region of the specified lung field and the characteristic amounts relating to the respiratory function of the entire lung field from the set measurement target region. Therefore, since it is possible to exclude from the measurement target a region including a signal unnecessary for calculation of the characteristic amount from the lung field region, it is possible to calculate the characteristic amount with high accuracy, and the prediction accuracy of the respiratory function value after the exclusion of the exclusion target portion is improved.

The controller 31 further displays the extracted lung field region and the set measurement target region on a preset one of the plurality of frame images so as to be identifiable, and when the contour of the lung field region or the measurement target region is corrected by the operation unit 33, the controller 31 corrects the predicted respiration function value based on the correction. Therefore, for example, it is possible to correct the automatically extracted lung field region or the measurement target region to an appropriate region.

The controller 31 highlights the exclusion target portion in the displayed frame image. Therefore, it is possible for the user to grasp the region recognized by the diagnostic console 3 as the exclusion target area.

The controller 31 displays a warning when the predicted respiration function value is within a preset range. Therefore, when the predicted respiration function value is within a preset range, (for example, a dangerous range), the user can easily recognize the fact.

Further, when the predicted respiration function value is within a preset range, the controller 31 causes the display 34 to display a display suggesting that the exclusion target portion should be reduced, so that the user can recognize that the reduction operation is necessary.

In addition, since the controller 31 recalculates the prediction rate and the respiratory function value when the exclusion target portion is reduced and displays them on the display 34, the user can easily recognize the predicted value of the respiratory function value when the reduction operation is performed.

When the information of the anatomical unit of the exclusion target portion is acquired from the electronic medical record system, the controller 31 calculates a prediction rate for predicting the respiratory function value when the exclusion target portion is excluded from the lung field, based on the acquired anatomical unit of the exclusion target portion. Therefore, it is possible to more easily designate the exclusion target portion.

Here, as a method for predicting the respiratory function after the operation, there is a method using a pulmonary blood flow scintigraphy examination. However, the pulmonary blood flow scintigraphy examination can only be held in a relatively large hospital and cannot be used in a small hospital because the scintigraphy examination apparatus is large and expensive. The pulmonary blood flow scintigraphy examination in facilities with the scintigraphy examination apparatus also requires waiting, usually about one week after ordering, for the management of radioisotopes. Further, the exposure is so great that it is used only in high-risk patients. Therefore, the risk of complications has not been accurately grasped in many patients.

In order to calculate the prediction rate of the respiratory function value from the image, it is necessary to specify at least the position of the lung field region from the image. However, since the images obtained by the pulmonary blood flow scintigraphy examination only obtain the right and left blood flow images, it is not possible to accurately grasp the extent of the lung field region. Therefore, it is necessary for the physician to manually set the lung field region on his/her own responsibility, and the prediction rate cannot be accurately calculated despite the labor.

On the other hand, according to the method of the present embodiment, since the dynamic image obtained by imaging the radiation image of the chest is used, the contour of the lung field region can be specified, and the prediction rate of the respiratory function value can be calculated with high accuracy. It is also possible to save the physician from the trouble of manually setting the lung field region. In order to predict respiratory function values from images obtained by pulmonary blood flow scintigraphy examination, images taken from two directions of ANT and POST need to be averaged, but by using moving images, images taken from one direction (e.g., ANT) need only be analyzed, thereby reducing process time.

That is, according to the present embodiment, on the basis of the dynamic image imaged by the radiation imaging apparatus that can be held in a general medical facility, it is possible to accurately calculate the prediction rate of the respiratory function value when the exclusion target portion is excluded without the user designating the range of the exclusion target portion from the two-dimensional image and while suppressing the load on the patient.

The description in the above embodiment is a preferred example of the present invention, and does not limit the present invention.

For example, in the embodiment described above, the case of predicting the respiratory function after the operation in the case where the respiratory function of the lung is excluded by excising a portion of the lung by operation has been described as an example, but the present invention is not limited to the case of resection, and may be applied to the case of predicting the respiratory function after the operation in the case where the respiratory function of the part is excluded by radiation therapy or laser irradiation.

In addition, in the above embodiment, the case where the prediction of the respiratory function after the operation is performed by performing the dynamic imaging before the operation has been described, however, the dynamic imaging may be performed after the operation to generate the blood flow characteristic amount image and the ventilation characteristic amount image based on the dynamic image after the operation, and the dynamic image after the operation, the blood flow characteristic amount image, and the ventilation characteristic amount image may be displayed on the respiratory function measurement screen 341 so that the actual movement of the lung after the operation can be observed. At this time, it is preferable to display a graph of changes in various measured values including the blood flow characteristic amount from the pre-operation. This makes the follow-up observation easier.

According to the above-described embodiment, the controller 31 has been described as specifying the lung field of the affected side based on the input anatomical unit of the exclusion target portion, designating the specified lung field region of the affected side as a partial region of the lung field for calculating the characteristic amount relating to the respiratory function, calculating the characteristic amount relating to the respiratory function in the lung field region of the affected side and the characteristic amount relating to the respiratory function of the entire lung field from a plurality of frame images, and calculating the prediction rate based on the value obtained by multiplying the ratio of the two calculated characteristic amounts by the ratio between the lung size value of the exclusion target portion and the lung size value of the affected lung field, but the method of calculating the prediction rate based on the anatomical unit of the input exclusion target portion is not limited to this.

For example, the region of the anatomical unit of the input exclusion target portion may be automatically extracted from a plurality of frame images, the extracted region may be specified as a partial region of the lung field for calculating the characteristic amount relating to the respiratory function, the characteristic amount relating to the respiratory function in the extracted region and the characteristic amount relating to the respiratory function of the entire lung field may be calculated, and the calculated value obtained by subtracting the calculated ratio of the two characteristic amounts from 1 may be calculated as the prediction rate. Alternatively, the region of the anatomical unit of the input exclusion target portion may be automatically extracted from a plurality of frame images, the region in which the extracted region is excluded from the entire lung field region may be specified as a partial region of the lung field for calculating the characteristic amount relating to the respiratory function, and the ratio of the characteristic amount relating to the respiratory function in the specified region and the characteristic amount relating to the respiratory function of the entire lung field may be calculated as the prediction rate. The respiratory function value predicted based on the prediction rate calculated by these methods can also be displayed on the respiratory function measurement screen 341 together with other information displayed on the respiratory function measurement screen 341, similarly to the respiratory function value predicted in the above embodiment.

When a calculated region of the characteristic amount is used as the anatomical unit of the level of the lobe-lung region, the three-dimensional position information of the lobe or lung region is stored in advance in the storage 32, and the corresponding position is mapped on the two-dimensional chest image in order to automatically extract the region.

For example, a chest is imaged in advance by the CT to acquire three-dimensional positional information of lung lobes and lung regions of a patient and the above is stored in the storage 32. Three-dimensional positional information is mapped so as to align with lung field edges and blood vessels on a two-dimensional chest image, whereby regions of lung lobes and lung regions on a two-dimensional chest image can be specified. As another method, a probability map (probability atlas) of three-dimensional positions of lung lobes and lung regions may be stored in the storage 32 based on CT imaging data of many patients, and three-dimensional position information formed by a probabilistic average value, a median value, or the like may be obtained and mapped.

After the three-dimensional position information is mapped onto the two-dimensional chest image, with respect to the handling of the region in which a plurality of lobe-lung regions overlap three-dimensionally, it is desirable that the exclusion target portion should be the exclusion target portion (the target of counting the characteristic amount) even if it overlaps with other lobe-lung regions, in order to estimate the respiratory function of the exclusion target portion to a large extent for safety. On the contrary, when overlapped with another lobe-lung region, it may be removed from the exclusion target portion, or the exclusion target portion may be set at an intermediate position or the like in accordance with the overlapping volume.

As a further alternative, a segmentation line may be drawn based on the ratio of distances from the lung field endpoints to extract regions (limited to lobectomy). For example, since the right lung has three lobes, upper, middle, and lower lobes, a line is set so as to be divided into three equal parts based on the upper end point and the lower end point of the lung field region, and based on this, the lung field region is divided into three parts to extract the calculated region of the characteristic amount. Since the left lung has two lobes, upper and lower lobes, it may be a half line or the like. The surgical information of the patient may be stored in the storage 32, and the calculated region of the characteristic amount may be extracted in consideration of the stored surgical information of the patient. For example, if the right upper lung has already been removed, the right lung may also be divided into two.

The points at the upper end and the lower end of the lung field region may be the uppermost end and the lowermost end of the lung field region. Here, the lung field region may or may not include the back of the diaphragm. It is desirable that the top and bottom ends of the lung field region are obtained from each of the right lung and the left lung, in order to handle patients with a left-right difference, but they may be obtained from both lungs. The ratio of each lung lobe does not have to be even, and may be changed based on, for example, the number of lung regions for each lung lobe or a probability map (probability atlas). The line may be set based on the position of various landmark structures such as a pulmonary artery, a pulmonary vein, and a branch point of a bronchus, in addition to the upper end and the lower end of the lung field region. The line may be straight or curved, or may be set along the course of the pulmonary vessel, etc.

As in the above embodiment, it is preferable that the calculated region of the characteristic amount is extracted from a measurement target region obtained by excluding a region with a large amount of noise or the like from the extracted lung field region.

Further, in the above embodiment, the lung field region and the measurement target region automatically extracted by the controller 31 are displayed on the representative frame image to which the color corresponding to the blood flow characteristic amount is added, and the contour of the lung field region and the measurement target region can be corrected from the displayed image by the operation of the operation unit 33. However, the image to which the automatically extracted lung field region and the measurement target region are displayed is not limited to this, and may be, for example, a representative frame image to which the color corresponding to the blood flow characteristic amount is not added. The same applies to an image in which the exclusion target portion is highlighted.

The above description discloses an example of using a hard disk, a semiconductor nonvolatile memory and the like as the computer readable medium including the program according to the present invention. However, the present invention is not limited to the example. For example, a portable storage medium such as a CD-ROM can be applied as the computer readable medium. A carrier wave is also applied as a medium providing the program data according to the present invention via a communication line.

As for the other detailed configurations and detailed operations of the dynamic analysis apparatus, modifications can be made as needed within the scope of the present invention.

Although embodiments of the present invention have been described and illustrated in detail, the disclosed embodiments are made for purposes of illustration and example only and not limitation. The scope of the present invention should be interpreted by terms of the appended claims.

What is claimed is:

1. A dynamic analysis apparatus comprising:
   a hardware processor configured to analyze a plurality of frame images showing a dynamic state of a chest portion of a subject and which calculates a prediction rate multiplied by a respiratory function value of the subject in predicting the respiratory function value when an exclusion target portion which is a portion of a lung field of the subject is excluded; and
   an input unit,
   wherein,
   the hardware processor obtains input of the exclusion target portion in an anatomical unit from the input unit,
   based on the anatomical unit obtained from the input unit, the hardware processor specifies a partial region of the lung field in which a characteristic amount relating to a respiratory function in the plurality of frame images is calculated,
   the hardware processor calculates the characteristic amount related to the respiratory function in the partial region of the lung field specified from the plurality of frame images and the characteristic amount related to the respiratory function of an entire lung field, and
   the hardware processor calculates the prediction rate based on a characteristic amount ratio which is a ratio of the two calculated characteristic amounts.

2. The dynamic analysis apparatus according to claim 1, wherein,
   the hardware processor obtains a respiratory function value of the entire lung of the subject, and
   the hardware processor predicts the respiratory function value when the exclusion target portion is excluded from the lung field by multiplying the prediction rate by the obtained respiratory function value.

3. The dynamic analysis apparatus according to claim 2, further comprising a display,
   wherein the hardware processor controls the display to display a predicted respiratory function value when the exclusion target portion is excluded from the lung field.

4. The dynamic analysis apparatus according to claim 3, wherein the hardware processor controls the display to display the characteristic amount ratio.

5. The dynamic analysis apparatus according to claim 3, wherein the hardware processor extracts left and right lung field regions from the plurality of frame images, sets a measurement target region in the extracted left and right lung field regions, and calculates the characteristic amount related to the respiratory function in the partial region of the lung field specified from the set measurement target region and the characteristic amount related to the respiratory function of the entire lung field.

6. The dynamic analysis apparatus according to claim 5, further comprising an operation unit,
wherein,
the hardware processor controls the display to display in a distinguishable manner the extracted lung field region and the set measurement target region on one frame image set in advance from among the plurality of frame images,
the hardware processor obtains a contour of the displayed lung field region or the displayed measurement target region which is corrected by operation on the operation unit, and
the hardware processor corrects the predicted respiratory function value based on correction of the contour of the lung field region or the measurement target region which is corrected on the operation unit.

7. The dynamic analysis apparatus according to claim 6, wherein the hardware processor controls the display to highlight the exclusion target portion in the displayed frame image.

8. The dynamic analysis apparatus according to claim 3, wherein the hardware processor controls the display to display a warning when the predicted respiratory function value is within a range set in advance.

9. The dynamic analysis apparatus according to claim 8, wherein the hardware processor controls the display to display a proposal to reduce the exclusion target portion when the predicted respiratory function value is within the range set in advance.

10. The dynamic analysis apparatus according to claim 9, wherein the hardware processor recalculates the prediction rate and the respiratory function value when the exclusion target portion is reduced and the hardware processor controls the display to display the prediction rate and the respiratory function value.

11. The dynamic analysis apparatus according to claim 1, wherein,
the hardware processor obtains information of the anatomical unit of the exclusion target portion from an electronic medical record system, and
when information of the anatomical unit of the exclusion target portion is obtained, the hardware processor calculates the prediction rate to predict the respiratory function value when the exclusion target portion is removed from the lung field based on the obtained information of the anatomical unit of the exclusion target portion.

12. The dynamic analysis apparatus according to claim 1, wherein the anatomical unit is any one of left or right, lobe, lung region, or lung sub-region.

13. The dynamic analysis apparatus according to claim 1, wherein the hardware processor specifies a lung field region on either a left or right side including the exclusion target portion as a partial region of the lung field in which the characteristic amount related to the respiratory function is calculated and calculates the characteristic amount ratio, obtains from a storage which stores in advance a lung size value for each anatomical unit included in the lung a lung size value of the anatomical unit corresponding to the exclusion target portion and a lung size value of the anatomical unit corresponding to the lung field on the side including the exclusion target portion, and based on the ratio of the obtained lung size value of the anatomical unit corresponding to the exclusion target portion and the obtained lung size value of the anatomical unit corresponding to the lung field on the side including the exclusion target portion multiplied by the characteristic amount ratio, the prediction rate is calculated.

14. A dynamic analysis system comprising:
an imaging apparatus which performs radiography on the subject to obtain a plurality of frame images showing a dynamic state of a chest portion of the subject; and
a dynamic analysis apparatus according to claim 1.

15. A non-transitory computer-readable storage medium storing a program which controls a computer used in a dynamic analysis apparatus the program which controls the computer to perform:
analyzing a plurality of frame images showing a dynamic state of a chest portion of a subject,
calculating a prediction rate multiplied to a respiratory function value of the subject in predicting the respiratory function value when an exclusion target portion which is a portion of a lung field of the subject is excluded,
obtaining input of the exclusion target portion in an anatomical unit,
based on the obtained anatomical unit, specifying a partial region of the lung field in which a characteristic amount relating to a respiratory function in the plurality of frame images is calculated,
calculating the characteristic amount related to the respiratory function in the partial region of the lung field specified from the plurality of frame images and the characteristic amount related to the respiratory function of an entire lung field, and
calculating the prediction rate based on a characteristic amount ratio which is a ratio of the two calculated characteristic amounts.

* * * * *